(12) United States Patent
Astles et al.

(10) Patent No.: US 8,252,798 B2
(45) Date of Patent: Aug. 28, 2012

(54) PURINE COMPOUNDS

(75) Inventors: Peter Charles Astles, Hampshire (GB);
Rossella Guidetti, Hampshire (GB);
Sean Patrick Hollinshead, Indianapolis, IN (US); Michael Wade Tidwell, Lakehills, TX (US)

(73) Assignee: Eli Lilly and Company, Indianapolis, IN (US)

( * ) Notice: Subject to any disclaimer, the term of this patent is extended or adjusted under 35 U.S.C. 154(b) by 349 days.

(21) Appl. No.: 12/633,812

(22) Filed: Dec. 9, 2009

(65) Prior Publication Data
US 2010/0160288 A1 Jun. 24, 2010

Related U.S. Application Data

(60) Provisional application No. 61/138,589, filed on Dec. 18, 2008.

(51) Int. Cl.
*C07D 473/34* (2006.01)
*C07D 519/00* (2006.01)
*A61K 31/52* (2006.01)
*A61P 25/04* (2006.01)
*C07D 473/40* (2006.01)
*C07D 403/12* (2006.01)
*C07D 407/12* (2006.01)
*C07D 409/12* (2006.01)

(52) U.S. Cl. .......... 514/252.16; 544/269; 544/277; 544/358; 544/264; 544/326; 544/329; 546/315; 514/249

(58) Field of Classification Search ............ 514/252.16, 514/249; 544/269, 277
See application file for complete search history.

(56) References Cited

U.S. PATENT DOCUMENTS

| 4,728,644 A | 3/1988 | Yuki et al. |
| 5,057,517 A * | 10/1991 | Johnston et al. ......... 514/252.16 |
| 2003/0139427 A1 | 7/2003 | Castelhano et al. |
| 2003/0153556 A1 * | 8/2003 | Levy et al. ..................... 514/218 |
| 2011/0245255 A1 * | 10/2011 | Sanderson et al. ............ 514/249 |

FOREIGN PATENT DOCUMENTS

| EP | 0300726 A1 | 1/1989 |
| WO | 03/022214 A2 | 3/2003 |
| WO | 2004/037823 A1 | 5/2004 |
| WO | 2005/067546 A2 | 7/2005 |
| WO | 2006/128172 A2 | 11/2006 |
| WO | WO 2011066211 A1 * | 6/2011 |

* cited by examiner

*Primary Examiner* — Mark Berch
(74) *Attorney, Agent, or Firm* — R. Craig Tucker

(57) ABSTRACT

A compound of the formula:

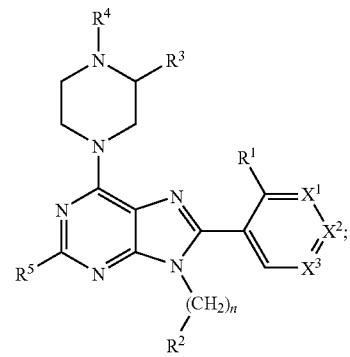

(I)

and pharmaceutical compositions for the treatment of pain.

19 Claims, No Drawings

PURINE COMPOUNDS

This U.S. regular patent applicaton claims priority under 35 U.S.C. §119(e) to U.S. provisional application Ser. No. 61/138,589, filed Dec. 18, 2008.

As a consequence of side effects associated with current oral pharmacological agents, there continues to be a need for the development of alternative therapies for the treatment of pain.

Cannabinoid receptors $CB_1$ and $CB_2$ belong to the class of G-protein-coupled receptors (GPCRs). $CB_1$ receptors are expressed both centrally and peripherally while $CB_2$ receptors are predominately expressed peripherally, primarily on immune cells and tissues.

The pharmacological and therapeutic potential of the $CB_2$ receptor has been reviewed recently (Br. J. Pharmacol. (2008) 153, 319-334) identifying $CB_2$ as a therapeutic target for the treatment of pain, in particular, inflammatory and neuropathic pain.

$CB_2$ agonists, in particular $CB_2$-selective agonists, provide a target for treating pain with limited centrally mediated side effects.

WO 2004/037823 is directed to purine compounds and use thereof as cannabinoid receptor ligands, in particular as $CB_1$ receptor antagonists.

The present invention provides a compound of the formula:

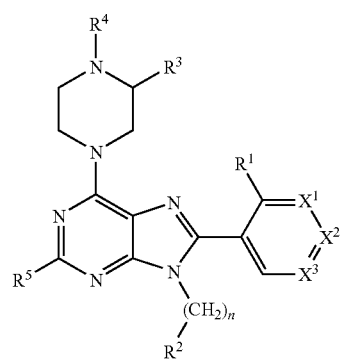

(I)

wherein;

$R^1$ is selected from H, F, Cl, $C_1$-$C_2$ alkyl, $CF_3$, cyclopropyl, $OCH_3$, $OCF_3$ and CN;

$R^2$ is selected from tetrahydrofuranyl, tetrahydropyranyl, azetidine-1-carboxylic acid methyl ester and tetrahydrothiophene-1,1-dioxide;

$R^3$ is H or combines with $R^4$ to form a fused pyrrolidin-2-one;

$R^4$ is selected from $C_1$-$C_2$ alkyl, $C_1$-$C_2$ fluoroalkyl, cyclopropyl and $COCH_3$;

$R^5$ is selected from H, $CH_3$ and $CF_3$;

n is 0 or 1;

$X^1$ and $X^3$ are independently selected from N, CH and $CR^6$;

$X^2$ is selected from CH and $CR^6$;

with the proviso that only one of $X^1$, $X^2$ and $X^3$ may be other than CH;

$R^6$ is selected from F, Cl, $CF_3$, $OCH_3$ and $OCF_3$;

or a pharmaceutically acceptable salt thereof.

The compounds of the present invention have been found to be agonists of the $CB_2$ receptor in vitro. Preferred compounds of the present invention exhibit greater potency than existing $CB_2$ agonists. More preferred compounds of the present invention are $CB_2$-selective agonists. Most preferred compounds of the present invention exhibit greater $CB_2$-selectivity than existing $CB_2$ agonists.

The present invention provides a pharmaceutical composition comprising a compound of the present invention, or a pharmaceutically acceptable salt thereof, and a pharmaceutically acceptable diluent or carrier.

The present invention provides a compound of Formula I, or a pharmaceutically acceptable salt thereof, for use in therapy. The present invention also provides the compound of Formula I, or a pharmaceutically acceptable salt thereof for use in the treatment of pain, in particular osteoarthritic pain. In another aspect of the present invention, there is provided the use of the compound of Formula I, or a pharmaceutically acceptable salt thereof, for the manufacture of a medicament for the treatment of pain, in particular osteoarthritic pain.

The present invention provides a method for the treatment of pain, which comprises administering an effective amount of a compound of Formula I, or a pharmaceutically acceptable salt thereof, to a human being or animal in need thereof. The present invention also provides a method for the treatment of osteoarthritic pain, which comprises administering an effective amount of a compound of Formula I, or a pharmaceutically acceptable salt thereof, to a human being or animal in need thereof.

The present invention provides a pharmaceutical composition for use in therapy comprising a compound of the present invention, or a pharmaceutically acceptable salt thereof. The present invention provides a pharmaceutical composition for use in pain, in particular osteoarthritic pain, comprising a compound of the present invention, or a pharmaceutically acceptable salt thereof.

It is preferred that the compounds of the present invention be used in the treatment of pain, in particular inflammatory pain, more particularly joint pain, most particularly osteoarthritic pain.

A preferred species of the compounds of the compounds of the present invention are compounds of the formula:

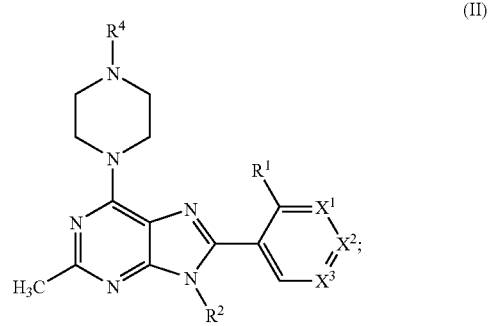

(II)

or a pharmaceutically acceptable salt thereof, wherein $R^1$, $R^2$, $R^4$, $X^1$, $X^2$ and $X^3$ are as defined herein.

A preferred species of the compounds of the compounds of the present invention are compounds of the formula:

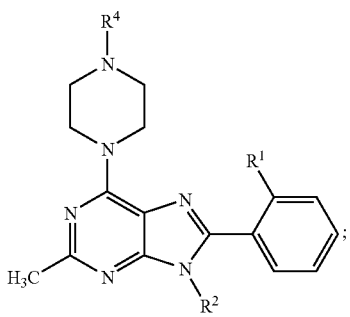
(III)

or a pharmaceutically acceptable salt thereof, wherein $R^1$, $R^2$ and $R^4$ are as defined herein.

Certain classes of compounds of Formula I, II or III are preferred. The following enumerated selections describe such preferred classes:
1) $R^1$ is Cl, $C_1$-$C_2$ alkyl, $CF_3$, cyclopropyl or $OCF_3$;
2) $R^1$ is Cl, methyl or ethyl;
3) $R^1$ is Cl;
4) $R^2$ is tetrahydrofuranyl or tetrahydropyranyl;
5) $R^2$ is tetrahydrofuranyl;
6) $R^2$ is tetrahydropyranyl;
7) $R^3$ is H;
8) $R^4$ is $C_1$-$C_2$ alkyl, $C_1$-$C_2$ fluoroalkyl or cyclopropyl;
9) $R^4$ is methyl, ethyl, 2-fluoroethyl or cyclopropyl;
10) $R^4$ is methyl or ethyl;
11) $R^5$ is $CH_3$;
12) $X^1$, $X^2$ and $X^3$ are independently selected from CH and $CR^6$ where $R^6$ is selected from Cl, $CF_3$, $OCH_3$ or $OCF_3$;
13) $X^1$, $X^2$ and $X^3$ are CH;
14) n is 0;
15) $R^3$ is H and $R^5$ is $CH_3$;
16) $R^1$ is Cl, methyl or ethyl; and $R^4$ is methyl, ethyl, 2-fluoroethyl or cyclopropyl;
17) $R^1$ is Cl, methyl or ethyl; $R^2$ is tetrahydrofuranyl or tetrahydropyranyl; and $R^4$ is methyl, ethyl, 2-fluoroethyl or cyclopropyl;
18) $R^1$ is Cl; $R^2$ is tetrahydrofuranyl or tetrahydropyranyl; and $R^4$ is methyl, ethyl, 2-fluoroethyl or cyclopropyl;
19) $R^1$ is Cl; $R^2$ is tetrahydrofuranyl or tetrahydropyranyl; and $R^4$ is methyl or ethyl;
20) $R^1$ is Cl; $R^2$ is tetrahydrofuranyl or tetrahydropyranyl; and $R^4$ is methyl or ethyl; $X^1$, $X^2$ and $X^3$ are independently selected from CH and $CR^6$ where $R^6$ is selected from Cl, $CF_3$, $OCH_3$ or $OCF_3$.

Pharmaceutically acceptable salts of each of the compounds of the present invention are contemplated within the scope of the present application.

Preferred compounds of the present invention include 8-(2-Chloro-pyridin-3-yl)-2-methyl-6-(4-methyl-piperazin-1-yl)-9-(R)-tetrahydro-furan-3-yl-9H-purine; 2-Methyl-6-(4-methyl-piperazin-1-yl)-9-(tetrahydro-pyran-4-yl)-8-(2-trifluoromethyl-phenyl)-9H-purine; 2-Methyl-6-(4-methyl-piperazin-1-yl)-9-(R)-tetrahydro-furan-3-yl-8-(2-trifluoromethyl-phenyl)-9H-purine; 2-Methyl-6-(4-methyl-piperazin-1-yl)-9-(R)-tetrahydro-furan-3-yl-8-o-tolyl-9H-purine; 8-(2-Chloro-phenyl)-2-methyl-6-(4-methyl-piperazin-1-yl)-9-(S)-tetrahydro-furan-3-yl-9H-purine; 8-(2-Chloro-phenyl)-2-methyl-6-(4-methyl-piperazin-1-yl)-9-(R)-tetrahydro-furan-3-yl-9H-purine; 8-(2-Chloro-phenyl)-2-methyl-6-(4-methyl-piperazin-1-yl)-9-(tetrahydro-pyran-4-yl)-9H-purine; and 8-(2-Chloro-phenyl)-6-(4-ethyl-piperazin-1-yl)-2-methyl-9-(tetrahydro-pyran-4-ylmethyl)-9H-purine; or a pharmaceutically acceptable salt thereof.

As used throughout this specification it is to be understood that where a group is qualified by "defined herein" or "herein defined" that said group encompasses the first occurring and broadest definition as well as each and all of the particular definitions of that group.

As used above and throughout the description of the invention, the following terms, unless otherwise indicated will have the following meaning:

As used herein the term $C_1$-$C_2$ alkyl refers to methyl or ethyl;

As used herein the term $C_1$-$C_2$ fluoroalkyl refers to a $C_1$-$C_2$ alkyl group as defined herein, wherein one or more hydrogen is replaced by fluorine and includes, trifluoromethyl, 2-fluoroethyl, 2,2-difluoroethyl and 2,2,2 trifluoroethyl. A preferred $C_1$-$C_2$ fluoroalkyl group is 2-fluoroethyl.

As used herein the term "pharmaceutically acceptable salt" refers to salts of the compounds of the present invention which are substantially non-toxic to living organisms. Such salts and common methodology for preparing them are well known in the art. See, e.g., P. Stahl, et al., Handbook of Pharmaceutical Salts: Properties Selection and Use, (VCHA/Wiley-VCH, 2002); and J. Pharm. Sci. 66, 2-19 (1977). Preferred pharmaceutically acceptable salts are hydrochloride and phosphate.

Embodiments of the invention include the examples provided herein, and although the example provided may be of one chiral or conformational form, or a salt thereof, further embodiments of the invention include all other steroisomeric and or conformational forms of the examples described, as well as pharmaceutically acceptable salts thereof.

As used herein the term "$CB_2$-selective agonists" or "$CB_2$-selectivity" refers to compounds having greater potency at $CB_2$ than $CB_1$. Preferred compounds of the present invention exhibit $\geq$100 fold $CB_2$-selectivity. More preferred compounds of the present invention exhibit $\geq$500 fold $CB_2$-selectivity. Most preferred compounds of the present invention exhibit $\geq$1000 fold $CB_2$-selectivity.

The compounds of the present invention are preferably formulated as pharmaceutical compositions administered by a variety of routes. Preferably, such compositions are for oral administration. Such pharmaceutical compositions and processes for preparing same are well known in the art. See, e.g., Remington: The Science and Practice of Pharmacy (A, Gennaro, et al., eds., 19th ed., Mack Publishing Co., 1995).

The following Schemes, Procedures and Examples are provided to better elucidate the practice of the present invention. Suitable reaction conditions for the steps of these Schemes, Procedures and Examples are well known in the art and appropriate modification of reaction conditions, including substitution of solvents and co-reagents are within the ability of the skilled artisan.

Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. The skilled artisan will appreciate that not all substituents are compatible with all reaction conditions. These compounds may be protected or modified at a convenient point in the synthesis by methods well known in the art.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "de-protection" of suitable protecting groups to be used by the skilled artisan.

The intermediates and final products of the present invention may be further purified, if desired by common techniques such as recrystallization or chromatography over solid supports such as silica gel or alumina.

The names for the compounds of the present invention are generated using AutoNom 2000.

Abbreviations used herein are defined as follows: "Brine" means a saturated aqueous sodium chloride solution; "BSA" means bovine serum albumin, "DDQ" means 2,3 dichloro-5,6-dicyano-1,4 benzoquinone; "DMEA" means N-Ethyldimethylamine; "EDTA" means ethylenediaminetetraaceticacid; "EtOH" means ethanol; "GCMS" means gas chromatography-mass spectrometry; "GDP" means guanosine diphosphate; "HEPES" means 4-(2-hydroxyethyl)-1-piperazineethanesulfonic acid; "IPA" means 2-propanol; "IPAm" means 2-propylamine; "L.R." means limiting reagent; "MeOH" means methanol; "PTSA" means para toluenesulfonic acid; "SCX" means a silica based strong cation exchange resin column, disposable cartridge or equivalent; "SFC" means supercritical fluid chromatography.

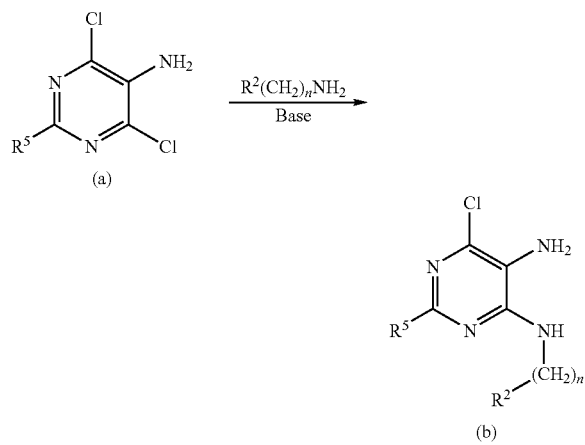

The starting pyrimidine (a) is reacted with an appropriately substituted amine and a suitable base such as diisopropylethylamine or triethylamine in a suitable solvent such as isopropanol at elevated temperature to provide compound (b).

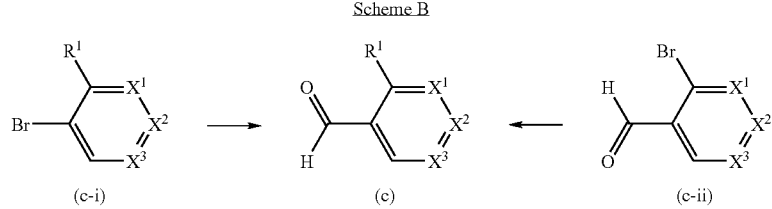

The starting bromide (c-i) is reacted with a strong base such as n-butyl lithium at reduced temperature and N,N-dimethylformamide in a suitable solvent such as anhydrous diethyl ether to provide compound (c).

Using Suzuki coupling conditions the starting aldehyde (c-ii) is reacted with a boronic acid derivative of $R^1$, a suitable catalyst such as (1,1'-bis(diphenylphosphino)ferrocene)palladium(II) chloride or $Pd(OAc)_2$ and a suitable base such as cesium fluoride in a suitable solvent such as 1,4-dioxane or toluene at elevated temperature to provide compound (c).

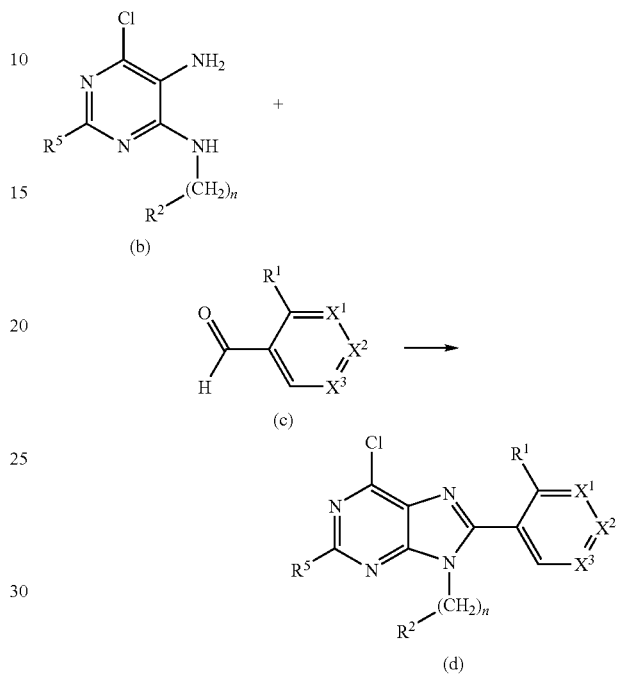

The starting pyrimidine (b) is reacted with aldehyde (c) (where $X^1$-$X^4$ is independently selected from CH and $CR^6$) and a suitable acid such as p-toluenesulfonic acid or 15% ferric chloride on silica in a suitable solvent such as 1,4-dioxane or toluene at elevated temperature. The reaction mixture is filtered and concentrated before reacting with DDQ in a suitable solvent such as dichloromethane at reduced temperature to provide purine (d).

The starting pyrimidine (b) is reacted with aldehyde (c) (where one of $X^1$-$X^4$ is N) and a suitable acid such as p-toluenesulfonic acid in a suitable solvent such as toluene at elevated temperature. The reaction mixture is filtered and concentrated before reacting with thionyl chloride at elevated temperature to provide purine (d).

General Procedure 2-1:
Heat a mixture of pyrimidine (b) (1.0 equiv., L.R.), aldehyde (c) (2.0 equiv.), and 15% ferric chloride on silica (200 wt. %, based on L.R.) in 1,4-dioxane to 100° C. for 16 hours. Cool and filter off the silica through diatomaceous earth, concentrate the filtrate under reduce pressure to give the resi due. Dissolve the residue in dry dichloromethane and add DDQ (1.0 equiv.) at 0° C. Allow to warm to room temperature with stirring. Upon reaction completion, dilute the reaction mixture with dichloromethane, wash with 15% aqueous sodium hydroxide, water, and brine. Dry the organic layer over anhydrous sodium sulfate, filter, and concentrate under reduced pressure to give the residue. Purify the residue by silica gel flash chromatography to give purine (d).

General Procedure 2-2:

Heat a solution of pyrimidine (b) (1.0 equiv., L.R.), aldehyde (c) (2 equiv.), p-toluenesulfonic acid (10 wt. %, based on L.R.), and molecular sieves (200 wt. %, based on L.R.) in toluene at reflux for 16 hours. Cool and filter off the molecular sieves through diatomaceous earth, concentrate the filtrate under reduced pressure to give the residue. Dissolve the residue in dry dichloromethane and add DDQ (1.0 equiv.) at 0° C. Allow to warm to room temperature and stir. Upon reaction completion, dilute the reaction mixture with dichloromethane, wash with 1N sodium hydroxide solution, water, and brine. Dry the organic layer over anhydrous sodium sulfate, filter, and concentrate under reduced pressure to give the residue. Purify the residue by silica gel flash chromatography to give purine (d).

General Procedure 2-3:

Charge a reaction vessel with the pyrimidine (b) (1.0 equiv., L.R.), aldehyde (c) (1.1 equiv.), toluene, and p-toluenesulfonic acid monohydrate (0.05 equiv.). Stir at 100° C. under nitrogen for 1 hour. Cool to room temperature, filter over diatomaceous earth, and concentrate under reduced pressure. Next, to the crude oil (imine) at room temperature under nitrogen add slowly thionyl chloride (neat/solvent). Stir at reflux for 30 minutes. Cool to room temperature and concentrate under reduced pressure. Add toluene and remove twice under reduced pressure. Dissolve in dichloromethane and basify slowly with saturated aqueous sodium bicarbonate. Dry the organic layer over anhydrous sodium sulfate, filter, and concentrate under reduced pressure. Purify by silica gel flash chromatography to give purine (d).

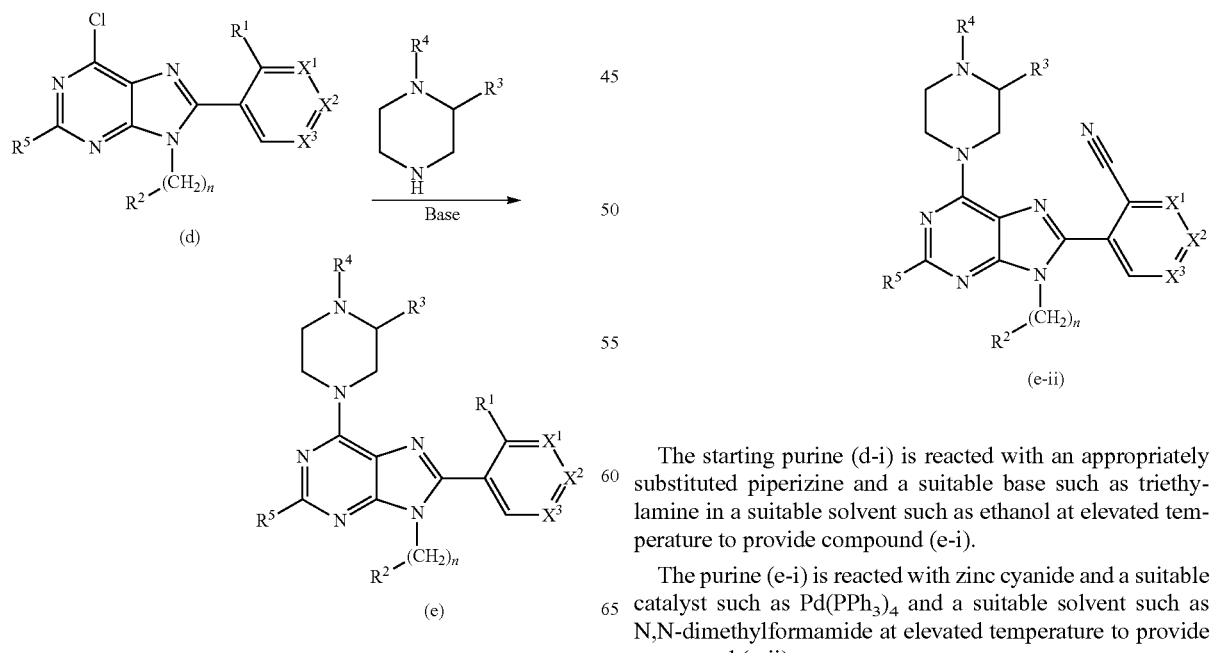

The starting purine (d) is reacted with an appropriately substituted piperizine and a suitable base such as triethylamine in a suitable solvent such as ethanol at elevated temperature to provide compound (e).

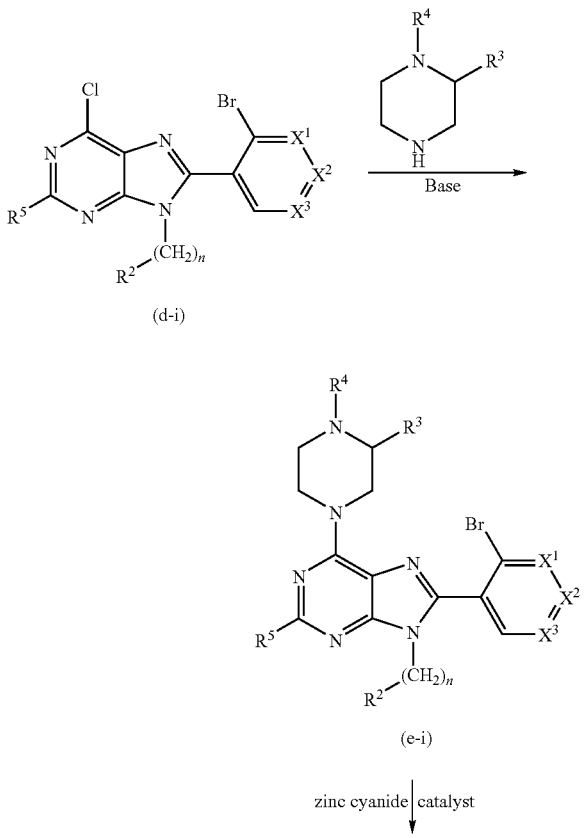

The starting purine (d-i) is reacted with an appropriately substituted piperizine and a suitable base such as triethylamine in a suitable solvent such as ethanol at elevated temperature to provide compound (e-i).

The purine (e-i) is reacted with zinc cyanide and a suitable catalyst such as Pd(PPh$_3$)$_4$ and a suitable solvent such as N,N-dimethylformamide at elevated temperature to provide compound (e-ii).

Scheme F

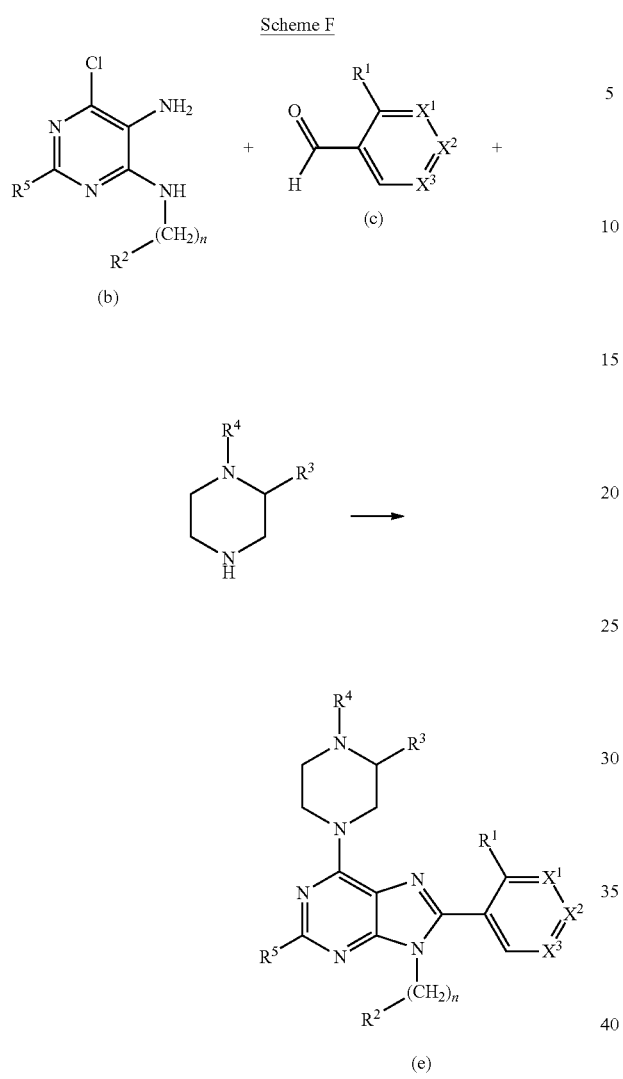

The starting pyrimidine (b) is reacted with aldehyde (c), an appropriately substituted piperizine and a suitable oxidant such as nitrobenzene or acetic acid in a suitable solvent such as methoxybenzene or dimethyl sulfoxide at elevated temperature to provide compound (e).

Scheme G

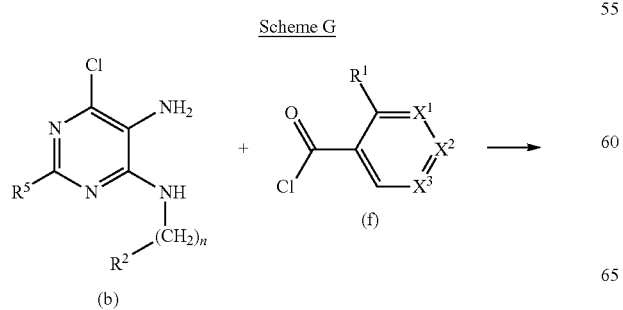

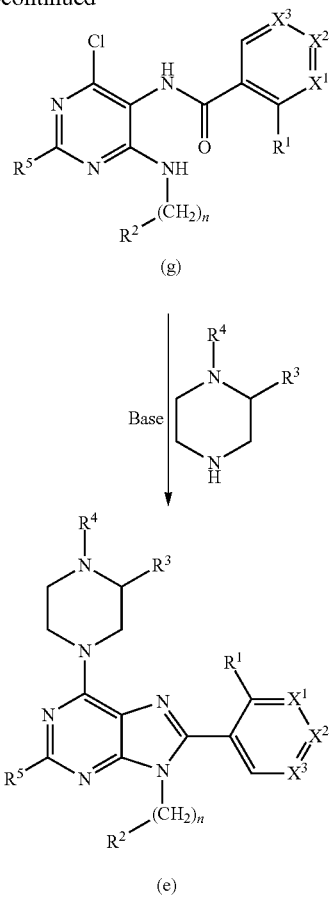

The starting pyrimidine (b) in a suitable solvent such as dimethylacetamide is reacted with an appropriately substituted acid chloride (f) at reduced temperature to provide compound (g).

The pyrimidine (g) in the presence of an appropriately substituted piperizine and a suitable base such as diisopropylethylamine in a suitable solvent such as isopropanol at elevated temperature and pressure to provide compound (e).

Preparation 1:

6-Chloro-2-methyl-N*4*-(tetrahydro-pyran-4-yl)-pyrimidine-4,5-diamine

Heat a solution of 4,6-Dichloro-2-methyl-pyrimidin-5-ylamine (0.008 mol, 1.5 g, 1.0 equiv.), 4-amino tetrahydropyran (0.012 mol, 1.27 g, 1.5 equiv.), and N,N-diisopropylethylamine (0.0092 mol, 1.1 g, 1.1 equiv.) in 2-propanol (80 mL) at 150° C. in a sealed tube for 16 hours. Cool the reaction mixture to room temperature and remove the 2-propanol under reduced pressure to give the residue. Dissolve the residue in dichloromethane and wash with water and brine. Dry the organic layer over anhydrous sodium sulfate, filter, and concentrate under reduced pressure to give a residue. Purify the residue on silica gel column eluting with dichloromethane: methanol 96:4 to give the title compound. MS (m/z): 243.41 (M+1).

Preparations 2-12 in Table 1 may be prepared essentially as described in Preparation 1 using the appropriate amine according to Scheme A.

TABLE 1

| Prep. No. | Structure | Chemical name | Physical data |
|---|---|---|---|
| 2 | 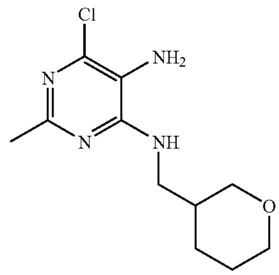 | 6-Chloro-2-methyl-N*4*(tetrahydro-pyran-3-ylmethyl)-pyrimidine-4,5-diamine | MS (m/z): 257 (M + 1) |
| 3 | 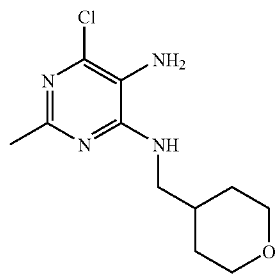 | 6-Chloro-2-methyl-N*4*(tetrahydro-pyran-4-ylmethyl)-pyrimidine-4,5-diamine | MS (m/z): 257 (M + 1) |
| 4 | 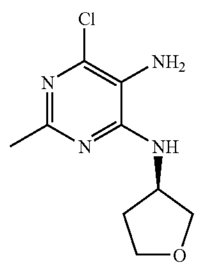 | 6-Chloro-2-methyl-N*4*-(R)-tetrahydro-furan-3-yl-pyrimidine-4,5-diamine | MS (m/z): 229 (M + 1) |
| 5 | 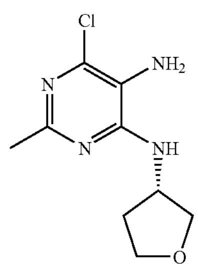 | 6-Chloro-2-methyl-N*4*-(S)-tetrahydro-furan-3-yl-pyrimidine-4,5-diamine | MS (m/z): 229 (M + 1) |
| 6 | 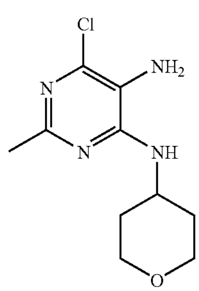 | 6-Chloro-2-methyl-N*4*-(tetrahydro-pyran-4-yl)-pyrimidine-4,5-diamine | MS (m/z): 243 (M + 1) |

TABLE 1-continued

| Prep. No. | Structure | Chemical name | Physical data |
|---|---|---|---|
| 7 | 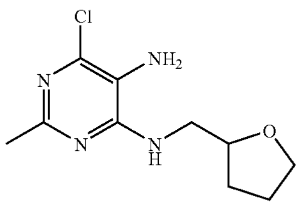 | 6-Chloro-2-methyl-N*4*-(tetrahydro-furan-2-ylmethyl)-pyrimidine-4,5-diamine | |
| 8 | 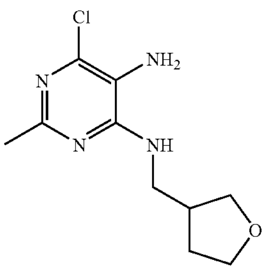 | 6-Chloro-2-methyl-N*4*-(tetrahydro-furan-3-ylmethyl)-pyrimidine-4,5-diamine | MS (m/z): 243 (M + 1) |
| 9 | 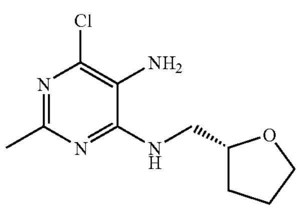 | 6-Chloro-2-methyl-N*4*-[(R)-1-(tetrahydro-furan-2-yl)methyl]-pyrimidine-4,5-diamine | MS (m/z): 243 (M + 1) |
| 10 | 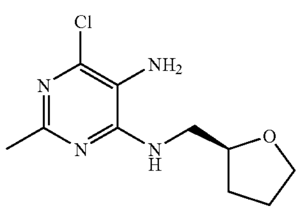 | 6-Chloro-2-methyl-N*4*-[(S)-1-(tetrahydro-furan-2-yl)methyl]-pyrimidine-4,5-diamine | MS (m/z): 243 (M + 1) |
| 11 | 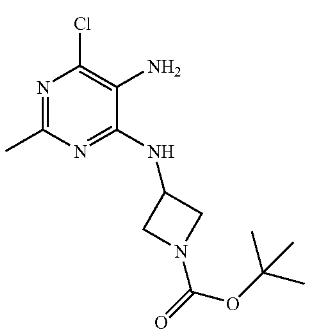 | 3-(5-Amino-6-chloro-2-methyl-pyrimidin-4-ylamino)-azetidine-1-carboxylic acid tert-butyl ester | MS (m/z): 314 (M + 1) |
| 12 | 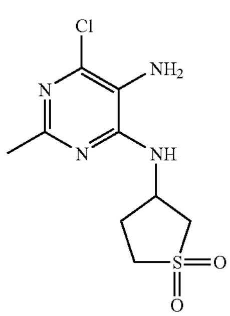 | 6-Chloro-N*4*-(1,1-dioxo-tetrahydro-1lambda*6*-thiophen-3-yl)-2-methyl-pyrimidine-4,5-diamine | MS (M/z): 277 (M + 1) |

Preparation 13:

2-Cyclopropyl-benzaldehyde

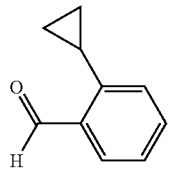

A 60 mL reaction vial is charged with 2-bromo-benzaldehyde (10.810 mmoles, 1.264 mL), cyclopropylboronic acid (14.053 mmoles, 1.207 g), potassium phosphate tribasic N-hydrate (37.834 mmoles, 8.031 g), tricyclohexylphosphine (1.081 mmoles, 303.139 mg), toluene (283.654 mmoles, 30.000 mL), and water (83.263 mmoles, 1.500 mL). The mixture is then thoroughly degassed. Next, Pd(OAc)$_2$ (540.482 μmoles, 121.343 mg) is added and the mixture is placed under nitrogen and heated to 100° C. After 2 hours, cool to room temperature and dilute with ethyl acetate (50 mL) and brine (50 mL). Dry the organic layer over anhydrous sodium sulfate, filter, and concentrate under reduced pressure. Purify by silica gel chromatography eluting with hexanes: dichloromethane 20-50% to afford the title compound. $^1$H NMR (400.31 MHz, cdcl3): 10.57 (s, 1H), 7.78 (dd, J=1.3, 7.9 Hz, 1H), 7.45 (td, J=7.5, 1.3 Hz, 1H), 7.28 (t, J=7.5 Hz, 1H), 7.09 (d, J=7.9 Hz, 1H), 2.63-2.56 (m, 1H), 1.07-1.02 (m, 2H), 0.77-0.73 (m, 2H).

Preparation 14:

2-Cyclopropyl-pyridine-3-carbaldehyde

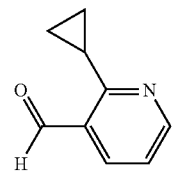

A 40 mL reaction vial is charged with 3 mL of 1,4-dioxane and a stirbar. Degas with nitrogen for 5 minutes. Next, the vial is charged with 2-bromonicotinaldehyde (645.134 μmoles, 120.000 mg), cyclopropylboronic acid (1.290 mmoles, 110.831 mg), and cesium fluoride (1.935 mmoles, 293.995 mg). The vial is then degassed again with nitrogen. Next, (1,1'-bis(diphenylphosphino)ferrocene)palladium(II) chloride (32.257 μmoles, 26.342 mg) is added and the reaction mixture is heated to 100° C. under nitrogen. Upon reaction completion, the mixture is cooled to room temperature, filtered over a pad of diatomaceous earth with ethyl acetate afford the title compound. GCMS (m/z): 146 (M).

Preparations 15-47 in Table 2 may be prepared using the appropriate substituted pyrimidine according to Scheme C and using the appropriate general procedure 2-1 through 2-3 as outlined in Table 2.

TABLE 2

| Prep. No. | Structure | Chemical name | Physical data | General Procedure |
|---|---|---|---|---|
| 15 | 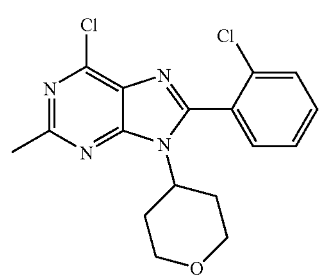 | 6-Chloro-8-(2-chloro-phenyl)-2-methyl-9-(tetrahydro-pyran-4-yl)-9H-purine | MS (m/z): 363 (M + 1) | 2-1 |
| 16 | 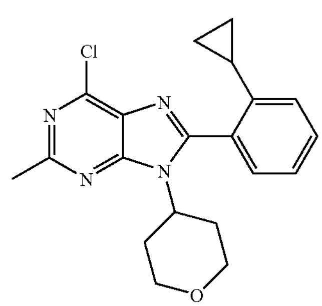 | 6-Chloro-8-(2-cyclopropyl-phenyl)-2-methyl-9-(tetrahydro-pyran-4-yl)-9H-purine | MS (m/z): 369 (M + 1) | 2-1 |

TABLE 2-continued

| Prep. No. | Structure | Chemical name | Physical data | General Procedure |
|---|---|---|---|---|
| 17 | 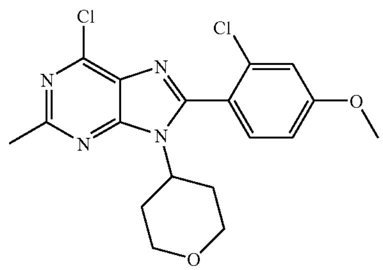 | 6-Chloro-8-(2-chloro-4-methoxy-phenyl)-2-methyl-9-(tetrahydro-pyran-4-yl)-9H-purine | MS (m/z): 393 (M + 1) | 2-1 |
| 18 | 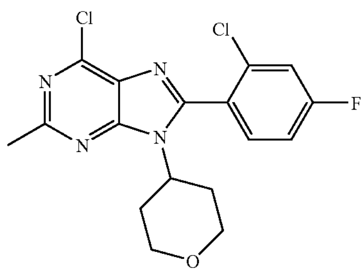 | 6-Chloro-8-(2-chloro-4-fluoro-phenyl)-2-methyl-9-(tetrahydro-pyran-4-yl)-9H-purine | MS (m/z): 381 (M + 1) | 2-1 |
| 19 | 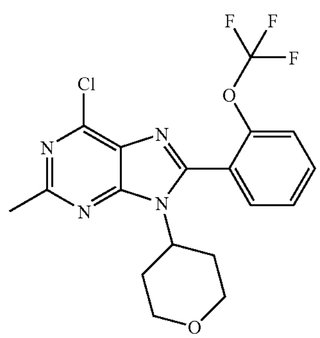 | 6-Chloro-2-methyl-9-(tetrahydro-pyran-4-yl)-8-(2-trifluoromethoxy-phenyl)-9H-purine | MS (m/z): 413 (M + 1) | 2-1 |
| 20 | 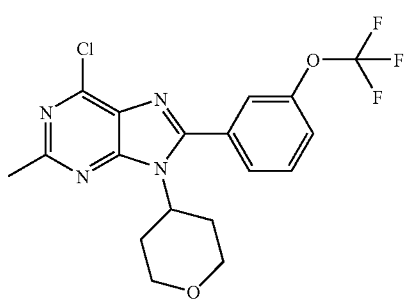 | 6-Chloro-2-methyl-9-(tetrahydro-pyran-4-yl)-8-(3-trifluoromethoxy-phenyl)-9H-purine | MS (m/z): 413 (M + 1) | 2-1 |
| 21 | 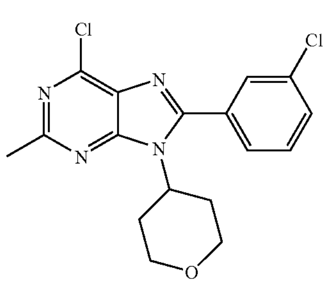 | 6-Chloro-8-(3-chloro-phenyl)-2-methyl-9-(tetrahydro-pyran-4-yl)-9H-purine | MS (m/z): 363 (M + 1) | 2-1 |

TABLE 2-continued

| Prep. No. | Structure | Chemical name | Physical data | General Procedure |
|---|---|---|---|---|
| 22 | 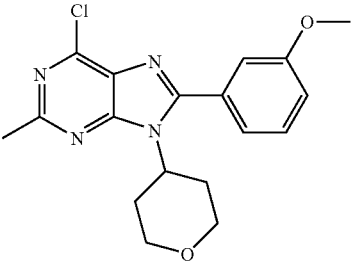 | 6-Chloro-8-(3-methoxy-phenyl)-2-methyl-9-(tetrahydro-pyran-4-yl)-9H-purine | MS (m/z): 359 (M + 1) | 2-1 |
| 23 | 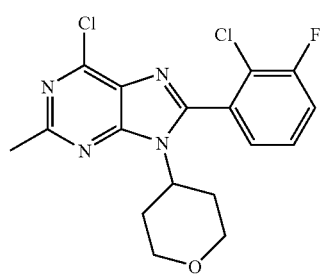 | 6-Chloro-8-(2-chloro-3-fluoro-phenyl)-2-methyl-9-(tetrahydro-pyran-4-yl)-9H-purine | MS (m/z): 381 (M + 1) | 2-1 |
| 24 | 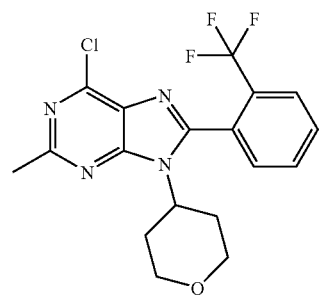 | 6-Chloro-2-methyl-9-(tetrahydro-pyran-4-yl)-8-(2-trifluoromethyl-phenyl)-9H-purine | MS (m/z): 397 (M + 1) | 2-1 |
| 25 | 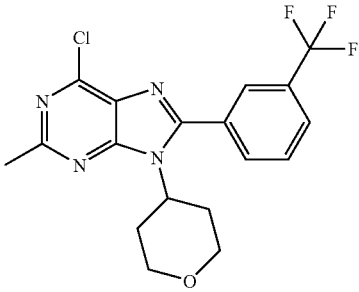 | 6-Chloro-2-methyl-9-(tetrahydro-pyran-4-yl)-8-(3-trifluoromethyl-phenyl)-9H-purine | MS (m/z): 397 (M + 1) | 2-1 |
| 26 | 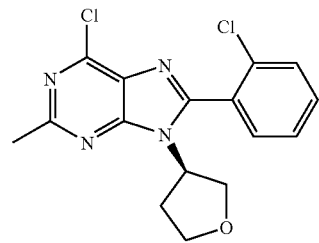 | 6-Chloro-8-(2-chloro-phenyl)-2-methyl-9-(R)-tetrahydro-furan-3-yl-9H-purine | MS (m/z): 349 (M + 1) | 2-1 |

TABLE 2-continued

| Prep. No. | Structure | Chemical name | Physical data | General Procedure |
|---|---|---|---|---|
| 27 | 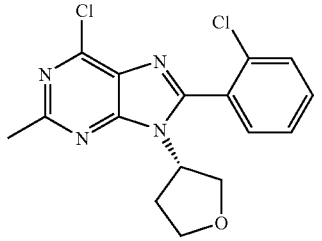 | 6-Chloro-8-(2-chloro-phenyl)-2-methyl-9-(S)-tetrahydro-furan-3-yl-9H-purine | MS (m/z): 349 (M + 1) | 2-1 |
| 28 | 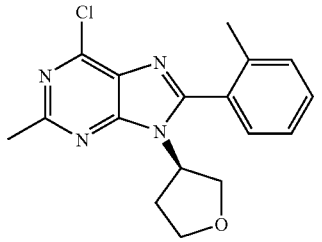 | 6-Chloro-2-methyl-9-(R)-tetrahydro-furan-3-yl-8-o-tolyl-9H-purine | MS (m/z): 329 (M + 1) | 2-1 |
| 29 | 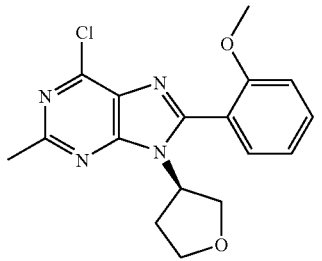 | 6-Chloro-8-(2-methoxy-phenyl)-2-methyl-9-(R)-tetrahydro-furan-3-yl-9H-purine | MS (m/z): 345 (M + 1) | 2-1 |
| 30 | 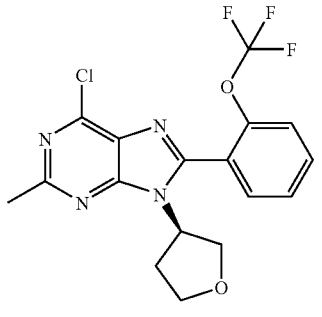 | 6-Chloro-2-methyl-9-(R)-tetrahydro-furan-3-yl-8-(2-trifluoromethoxy-phenyl)-9H-purine | MS (m/z): 399 (M + 1) | 2-1 |
| 31 | 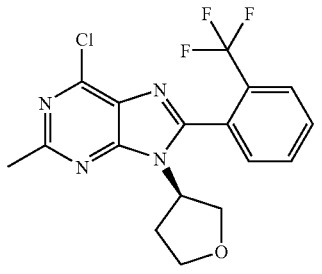 | 6-Chloro-2-methyl-9-(R)-tetrahydro-furan-3-yl-8-(2-trifluoromethyl-phenyl)-9H-purine | MS (m/z): 385 (M + 1) | 2-1 |

TABLE 2-continued

| Prep. No. | Structure | Chemical name | Physical data | General Procedure |
|---|---|---|---|---|
| 32 | 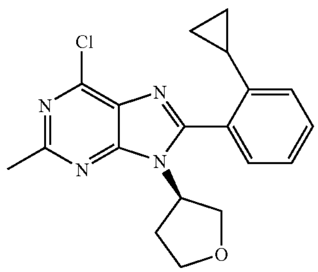 | 6-Chloro-8-(2-cyclopropyl-phenyl)-2-methyl-9-(R)-tetrahydro-furan-3-yl-9H-purine | MS (m/z): 355 (M + 1) | 2-1 |
| 33 | 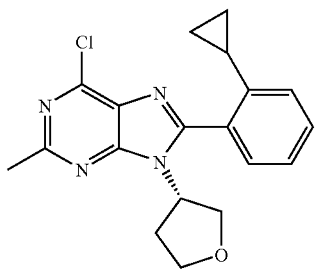 | 6-Chloro-8-(2-cyclopropyl-phenyl)-2-methyl-9-(S)-tetrahydro-furan-3-yl-9H-purine | MS (m/z): 355 (M + 1) | 2-1 |
| 34 | 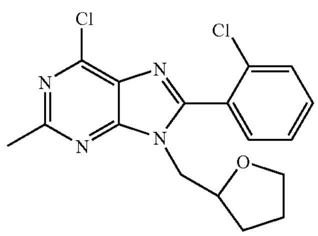 | 6-Chloro-8-(2-chloro-phenyl)-2-methyl-9-(tetrahydro-furan-2-ylmethyl)-9H-purine | MS (m/z): 363 (M + 1) | 2-1 |
| 35 | 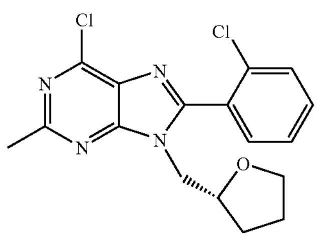 | 6-Chloro-8-(2-chloro-phenyl)-2-methyl-9-[(R)-1-(tetrahydro-furan-2-yl)methyl]-9H-purine | MS (m/z): 363 (M + 1) | 2-1 |
| 36 | 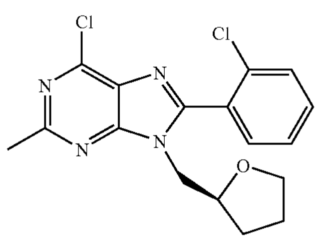 | 6-Chloro-8-(2-chloro-phenyl)-2-methyl-9-[(S)-1-(tetrahydro-furan-2-yl)methyl]-9H-purine | MS (m/z): 363 (M + 1) | 2-1 |
| 37 | 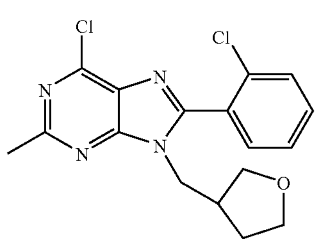 | 6-Chloro-8-(2-chloro-phenyl)-2-methyl-9-(tetrahydro-furan-3-ylmethyl)-9H-purine | MS (m/z): 363 (M + 1) | 2-2 |

TABLE 2-continued

| Prep. No. | Structure | Chemical name | Physical data | General Procedure |
|---|---|---|---|---|
| 38 | 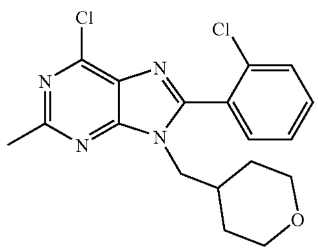 | 6-Chloro-8-(2-chloro-phenyl)-2-methyl-9-(tetrahydro-pyran-4-ylmethyl)-9H-purine | MS (m/z): 377 (M + 1) | 2-2 |
| 39 | 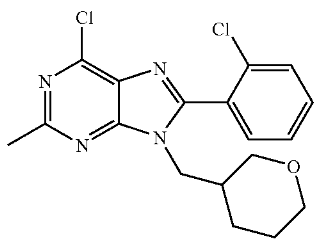 | 6-Chloro-8-(2-chloro-phenyl)-2-methyl-9-(tetrahydro-pyran-3-ylmethyl)-9H-purine | MS (m/z): 377 (M + 1) | 2-1 |
| 40 | 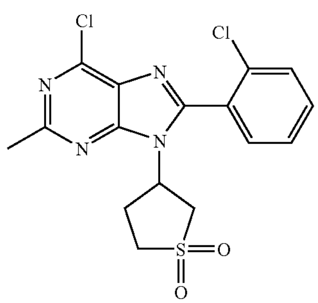 | 6-Chloro-8-(2-chloro-phenyl)-9-(1,1-dioxo-tetrahydro-1lambda*6*-thiophen-3-yl)-2-methyl-9H-purine | MS (m/z): 397 (M + 1) | 2-1 |
| 41 | 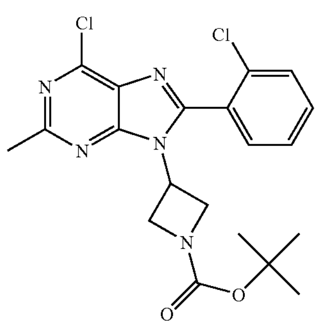 | 3-[6-Chloro-8-(2-chloro-phenyl)-2-methyl-purin-9-yl]-azetidine-1-carboxylic acid tert-butyl ester | MS (m/z): 434 (M + 1) | 2-2 |
| 42 | 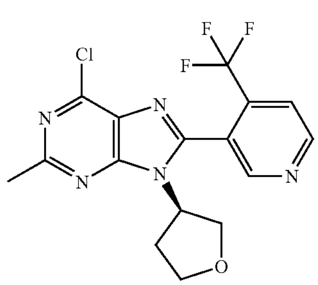 | 6-Chloro-2-methyl-9-(R)-tetrahydro-furan-3-yl-8-(4-trifluoromethyl-pyridin-3-yl)-9H-purine | MS (m/z): 384 (M + 1) | 2-3 |

TABLE 2-continued

| Prep. No. | Structure | Chemical name | Physical data | General Procedure |
|---|---|---|---|---|
| 43 | 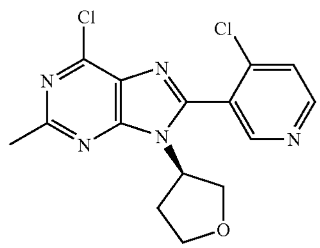 | 6-Chloro-8-(4-chloro-pyridin-3-yl)-2-methyl-9-(R)-tetrahydro-furan-3-yl-9H-purine | MS (m/z): 352 (M + 1) | 2-3 |
| 44 | 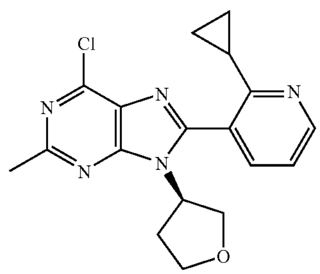 | 6-Chloro-8-(2-cyclopropyl-pyridin-3-yl)-2-methyl-9-(R)-tetrahydro-furan-3-yl-9H-purine | MS (m/z): 356 (M + 1) | 2-3 |
| 45 | 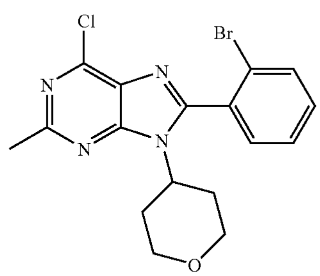 | 8-(2-Bromo-phenyl)-6-chloro-2-methyl-9-(tetrahydro-pyran-4-yl)-9H-purine | MS (m/z): 409 (M + 1) | 2-1 |
| 46 | 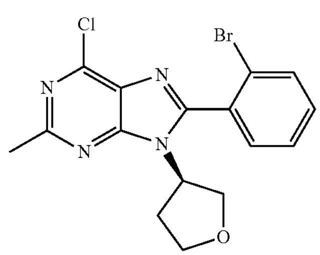 | 8-(2-Bromo-phenyl)-6-chloro-2-methyl-9-(R)-tetrahydro-furan-3-yl-9H-purine | MS (m/z): 393 (M + 1) | 2-1 |
| 47 | 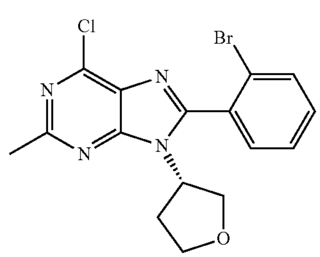 | 8-(2-Bromo-phenyl)-6-chloro-2-methyl-9-(S)-tetrahydro-furan-3-yl-9H-purine | MS (m/z): 393 (M + 1) | 2-2 |

Preparation 48:

6-Chloro-8-(2-chloro-pyridin-3-yl)-2-methyl-9-(R)-tetrahydro-furan-3-yl-9H-purine

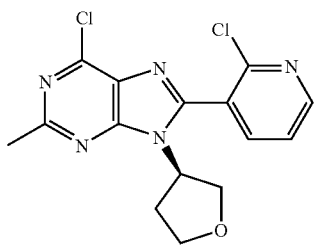

Charge a reaction vessel with R-6-Chloro-2-methyl-N4-(tetrahydro-furan-3-yl)-pyrimidine-4,5-diamine (2.186 mmoles, 500.000 mg), 2-bromonicotinaldehyde (3.280 mmoles, 610.046 mg), toluene (94.551 mmoles, 10.000 mL), and PTSA monohydrate (109.323 μmoles, 20.795 mg). Heat at 100° C. under nitrogen for 1 hour. Cool to room temperature, filter, and concentrate under reduced pressure. Next, to the crude oil (imine) at room temperature under nitrogen add slowly thionyl chloride (68.630 mmoles, 5.000 mL). Heat to 80° C. for 30 minutes. Concentrate under reduced pressure. Add toluene (~10 mL) and remove twice under reduced pressure. Dissolve the residue in dichloromethane and basify slowly with saturated aqueous sodium bicarbonate. Dry the organic layer over anhydrous sodium sulfate, filter, and concentrate under reduced pressure. Purify by silica gel chromatography eluting with hexanes: acetone to afford the title compound. (648 mg). MS (m/z): 350 (M+1).

Preparation 49:

1-(2-Fluoro-ethyl)-piperazine hydrochloride salt

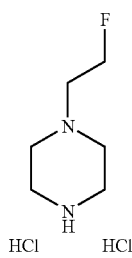

Step 1:

Charge a reaction vessel with N-tert-butoxycarbonylpiperazine (8.590 mmoles, 1.600 g), potassium carbonate (25.771 mmoles, 3.562 g), sodium iodide (cat.) (66.714 μmoles, 10.000 mg), 1,4-dioxane (234.262 mmoles, 20.000 mL), 1-bromo-2-fluoroethane (9.449 mmoles, 704.029 μL), and a stirbar. Heat with stirring overnight at reflux. Upon reaction completion, cool to room temperature and concentrate under reduced pressure. Partition with ethyl acetate and water. Separate the organic layer and dry over anhydrous sodium sulfate, filter, and concentrate under reduced pressure to afford pure 4-(2-fluoro-ethyl)-piperazine-1-carboxylic acid tert-butyl ester. GCMS (m/z): 232 (M).

Step 2:

Add 4N HCl in 1,4-dioxane (86.096 mmoles, 21.524 mL) to a stirred solution of 4-(2-fluoro-ethyl)-piperazine-1-carboxylic acid tert-butyl ester (8.610 mmoles, 2.000 g) in dry dichloromethane (60 mL) at room temperature under nitrogen. Stir overnight under nitrogen. Concentrate under reduced pressure to afford the title compound (8.679 mmoles, 1.780 g). MS (m/z): 133 (M+1).

EXAMPLE 1

8-(2-Chloro-phenyl)-6-(4-ethyl-piperazin-1-yl)-2-methyl-9-(tetrahydro-pyran-4-yl)-9H-purine hydrochloride salt

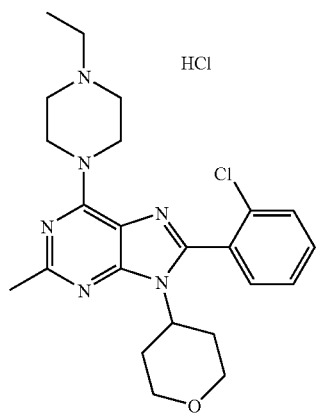

Heat a solution of 6-chloro-8-(2-chlorophenyl)-2-methyl-9-(tetrahydro-2H-pyran-4-yl)-9H-purine (0.0005 mol, 0.2 g), N-ethyl piperazine (0.0006 mol, 0.069 g, 1.1 equiv.), and triethylamine (0.0006 mol, 0.061 g, 1.1 equiv.) in ethanol (5.0 mL) at reflux for 20 hours. Alternatively, heat the reaction with microwave irradiation. Upon reaction completion, concentrate the reaction mixture under reduced pressure. Dissolve the residue in dry dichloromethane and wash with saturated sodium bicarbonate solution, water, and brine. Dry the organic layer over anhydrous sodium sulfate, filter, and concentrate under reduced pressure to give the residue. Purify by silica gel chromatography eluting with hexanes:acetone 90:10 to give the freebase. Add HCl (2M solution in ethanol) (1.0 equiv.) to the freebase (0.23 g, 0.500 mmol) in diethyl ether (5 mL) at 0° C. and stir for 2 hours at room temperature. Filter and wash precipitate with diethyl ether. Dry the precipitate under vacuum to give the title compound (0.2 g). MS (m/z): 441.28 (M+1). Alternatively, prepare the HCl salt by dissolving the freebase in acetone, 1:1 acetonitrile:water, or another suitable organic solvent, then add with stirring a solution of aqueous or ethereal HCl. Then lyophilize to afford the hydrochloride salt.

Examples 2-72 in Table 3 may be prepared essentially as described in Example 1 using the appropriately substituted purine and the appropriately substituted piperazine according to Scheme D.

TABLE 3

| Example No. | Structure | Chemical name | Physical data |
|---|---|---|---|
| 2 | 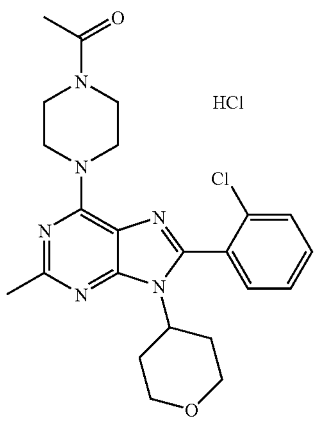 | 1-{4-[8-(2-Chloro-phenyl)-2-methyl-9-(tetrahydro-pyran-4-yl)-9H-purin-6-yl]-piperazin-1-yl}-ethanone hydrochloride salt | MS (m/z): 455 (M + 1) |
| 3 | 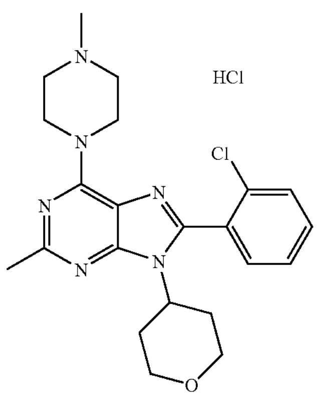 | 8-(2-Chloro-phenyl)-2-methyl-6-(4-methyl-piperazin-1-yl)-9-(tetrahydro-pyran-4-yl)-9H-purine hydrochloride salt | MS (m/z): 427 (M + 1) |
| 4 | 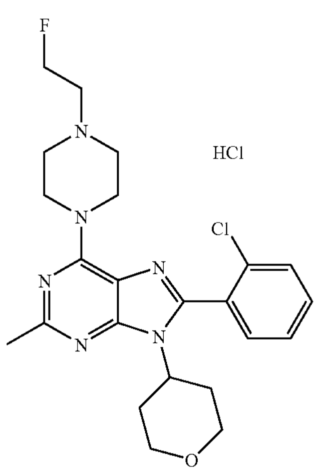 | 8-(2-Chloro-phenyl)-6-[4-(2-fluoro-ethyl)-piperazin-1-yl]-2-methyl-9-(tetrahydro-pyran-4-yl)-9H-purine hydrochloride salt | MS (m/z): 459 (M + 1) |

TABLE 3-continued

| Example No. | Structure | Chemical name | Physical data |
|---|---|---|---|
| 5 | 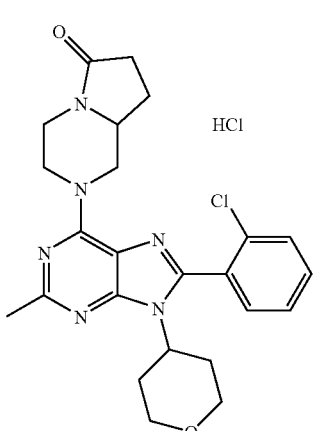 | 2-[8-(2-Chloro-phenyl)-2-methyl-9-(tetrahydro-pyran-4-yl)-9H-purin-6-yl]-hexahydro-pyrrolo[1,2-a]pyrazin-6-one hydrochloride salt, Isomer 2[a] | MS (m/z): 425 (M + 1) |
| 6 | 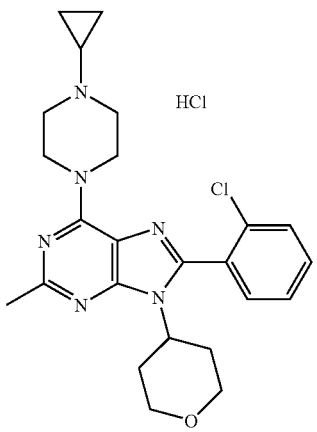 | 8-(2-Chloro-phenyl)-6-(4-cyclopropyl-piperazin-1-yl)-2-methyl-9-(tetrahydro-pyran-4-yl)-9H-purine hydrochloride salt | MS (m/z): 453 (M + 1) |
| 7 | 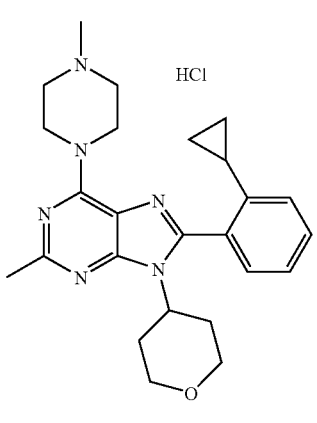 | 8-(2-Cyclopropyl-phenyl)-2-methyl-6-(4-methyl-piperazin-1-yl)-9-(tetrahydro-pyran-4-yl)-9H-purine hydrochloride salt | MS (m/z): 433 (M + 1) |

TABLE 3-continued

| Example No. | Structure | Chemical name | Physical data |
|---|---|---|---|
| 8 | 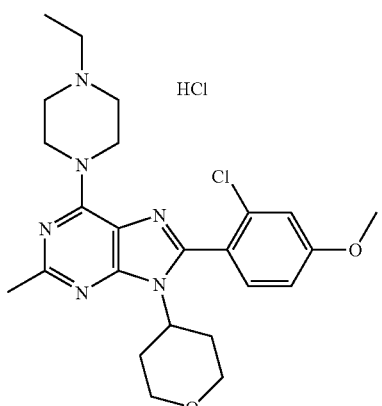 | 8-(2-Chloro-4-methoxy-phenyl)-6-(4-ethyl-piperazin-1-yl)-2-methyl-9-(tetrahydro-pyran-4-yl)-9H-purine hydrochloride salt | MS (m/z): 471 (M + 1) |
| 9 | 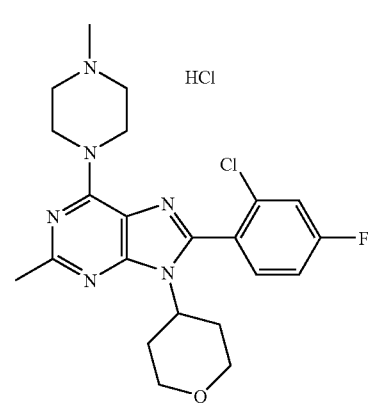 | 8-(2-Chloro-4-fluoro-phenyl)-2-methyl-6-(4-methyl-piperazin-1-yl)-9-(tetrahydro-pyran-4-yl)-9H-purine hydrochloride salt | MS (m/z): 455 (M + 1) |
| 10 | 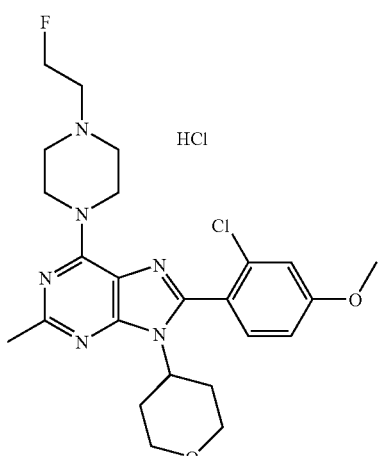 | 8-(2-Chloro-4-methoxy-phenyl)-6-[4-(2-fluoro-ethyl)-piperazin-1-yl]-2-methyl-9-(tetrahydro-pyran-4-yl)-9H-purine hydrochloride salt | MS (m/z): 489 (M + 1) |

TABLE 3-continued

| Example No. | Structure | Chemical name | Physical data |
|---|---|---|---|
| 11 | 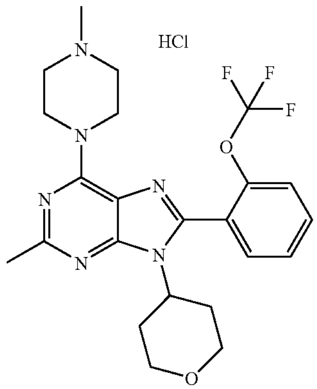 | 2-Methyl-6-(4-methyl-piperazin-1-yl)-9-(tetrahydro-pyran-4-yl)-8-(2-trifluoromethoxy-phenyl)-9H-purine hydrochloride salt | MS (m/z): 477 (M + 1) |
| 12 | 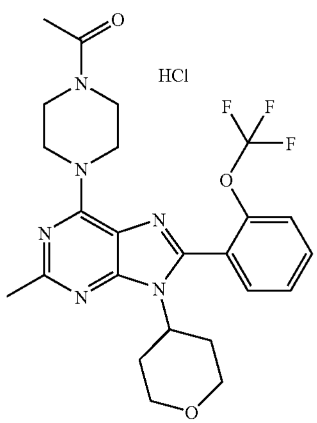 | 1-{4-[2-Methyl-9-(tetrahydro-pyran-4-yl)-8-(2-trifluoromethoxy-phenyl)-9H-purin-6-yl]-piperazin-1-yl}-ethanone hydrochloride salt | MS (m/z): 505 (M + 1) |
| 13 | 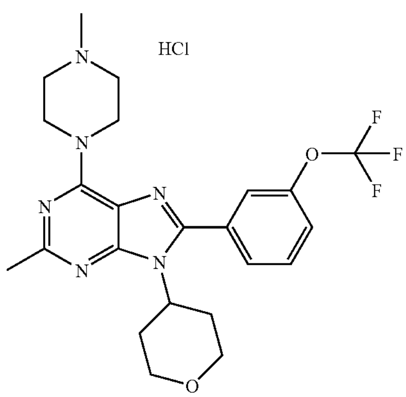 | 2-Methyl-6-(4-methyl-piperazin-1-yl)-9-(tetrahydro-pyran-4-yl)-8-(3-trifluoromethoxy-phenyl)-9H-purine hydrochloride salt | MS (m/z): 477 (M + 1) |
| 14 | 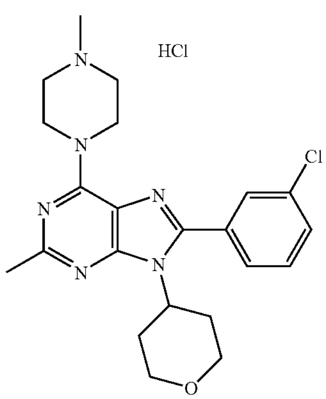 | 8-(3-Chloro-phenyl)-2-methyl-6-(4-methyl-piperazin-1-yl)-9-(tetrahydro-pyran-4-yl)-9H-purine hydrochloride salt | MS (m/z): 427 (M + 1) |

TABLE 3-continued

| Example No. | Structure | Chemical name | Physical data |
|---|---|---|---|
| 15 | 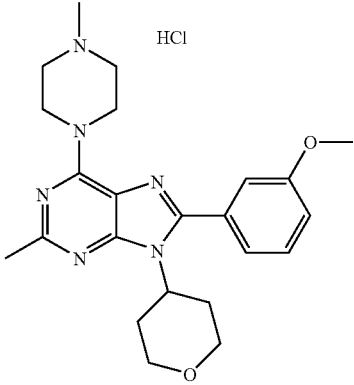 | 8-(3-Methoxy-phenyl)-2-methyl-6-(4-methyl-piperazin-1-yl)-9-(tetrahydro-pyran-4-yl)-9H-purine hydrochloride salt | MS (m/z): 423 (M + 1) |
| 16 | 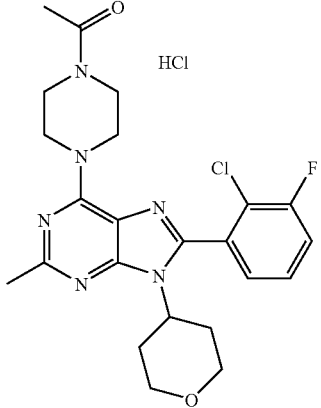 | 1-{4-[8-(2-Chloro-3-fluoro-phenyl)-2-methyl-9-(tetrahydro-pyran-4-yl)-9H-purin-6-yl]-piperazin-1-yl}-ethanone hydrochloride salt | MS (m/z): 473 (M + 1) |
| 17 | 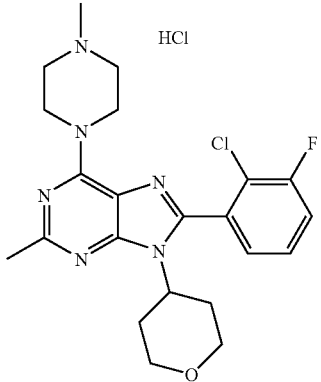 | 8-(2-Chloro-3-fluoro-phenyl)-2-methyl-6-(4-methyl-piperazin-1-yl)-9-(tetrahydro-pyran-4-yl)-9H-purine hydrochloride salt | MS (m/z): 445 (M + 1) |

TABLE 3-continued

| Example No. | Structure | Chemical name | Physical data |
|---|---|---|---|
| 18 | 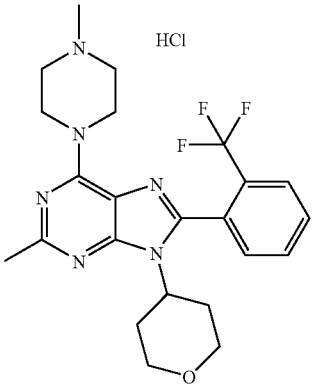 | 2-Methyl-6-(4-methyl-piperazin-1-yl)-9-(tetrahydro-pyran-4-yl)-8-(2-trifluoromethyl-phenyl)-9H-purine hydrochloride salt | MS (m/z): 461 (M + 1) |
| 19 | 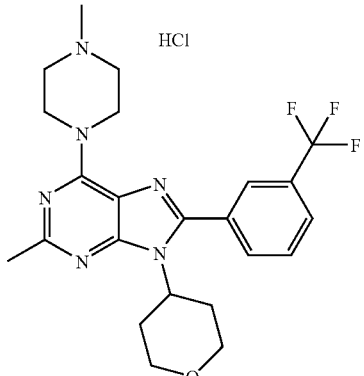 | 2-Methyl-6-(4-methyl-piperazin-1-yl)-9-(tetrahydro-pyran-4-yl)-8-(3-trifluoromethyl-phenyl)-9H-purine hydrochloride salt | MS (m/z): 461 (M + 1) |
| 20 | 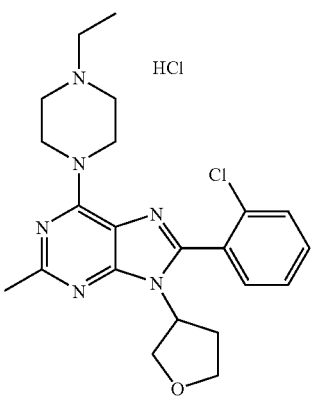 | 8-(2-Chloro-phenyl)-6-(4-ethyl-piperazin-1-yl)-2-methyl-9-(tetrahydro-furan-3-yl)-9H-purine hydrochloride salt, Isomer 1[b] | MS (m/z): 427 (M + 1) |
| 21 | 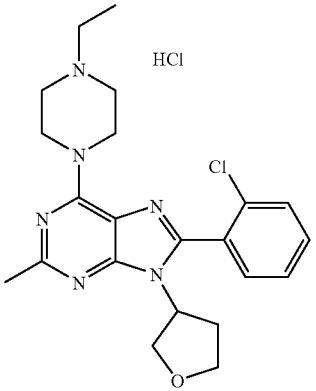 | 8-(2-Chloro-phenyl)-6-(4-ethyl-piperazin-1-yl)-2-methyl-9-(tetrahydro-furan-3-yl)-9H-purine hydrochloride salt, Isomer 2[b] | MS (m/z): 427 (M + 1) |

TABLE 3-continued

| Example No. | Structure | Chemical name | Physical data |
|---|---|---|---|
| 22 | 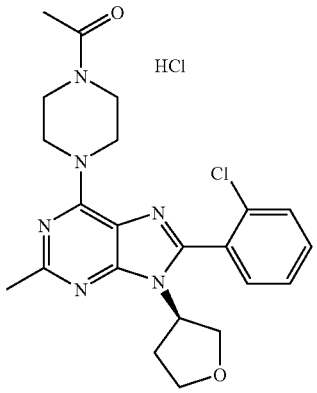 | 1-{4-[(R)-8-(2-Chloro-phenyl)-2-methyl-9-tetrahydro-furan-3-yl-9H-purin-6-yl]-piperazin-1-yl}-ethanone hydrochloride salt | MS (m/z): 441 (M + 1) |
| 23 | 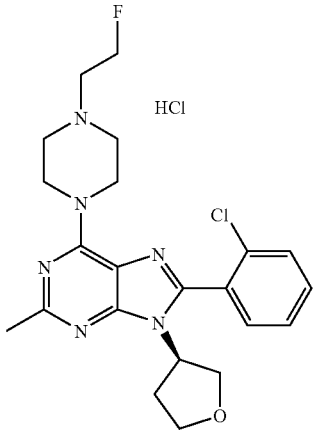 | 8-(2-Chloro-phenyl)-6-[4-(2-fluoro-ethyl)-piperazin-1-yl]-2-methyl-9-(R)-tetrahydro-furan-3-yl-9H-purine hydrochloride salt | MS (m/z): 445 (M + 1) |
| 24 | 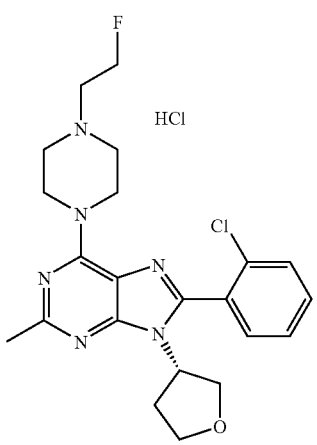 | 8-(2-Chloro-phenyl)-6-[4-(2-fluoro-ethyl)-piperazin-1-yl]-2-methyl-9-(S)-tetrahydro-furan-3-yl-9H-purine hydrochloride salt | MS (m/z): 445 (M + 1) |

TABLE 3-continued

| Example No. | Structure | Chemical name | Physical data |
|---|---|---|---|
| 25 | 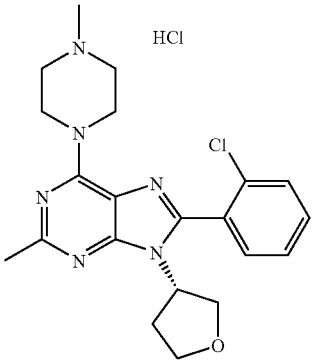 | 8-(2-Chloro-phenyl)-2-methyl-6-(4-methyl-piperazin-1-yl)-9-(S)-tetrahydro-furan-3-yl-9H-purine hydrochloride salt | MS (m/z): 413 (M + 1) |
| 26 | 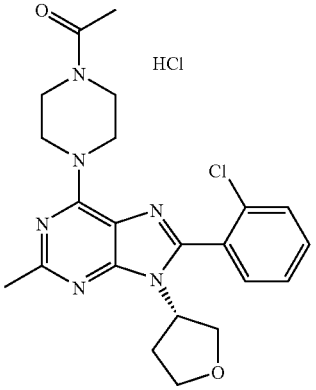 | 1-{4-[(S)-8-(2-Chloro-phenyl)-2-methyl-9-tetrahydro-furan-3-yl-9H-purin-6-yl]-piperazin-1-yl}-ethanone hydrochloride salt | MS (m/z): 441 (M + 1) |
| 27 | 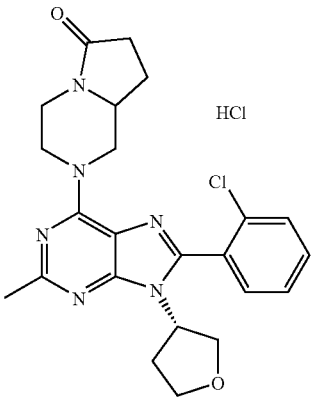 | 2-[(S)-8-(2-Chloro-phenyl)-2-methyl-9-tetrahydro-furan-3-yl-9H-purin-6-yl]-hexahydro-pyrrolo[1,2-a]pyrazin-6-one hydrochloride salt, Isomer 1[c] | MS (m/z): 453 (M + 1) |
| 28 | 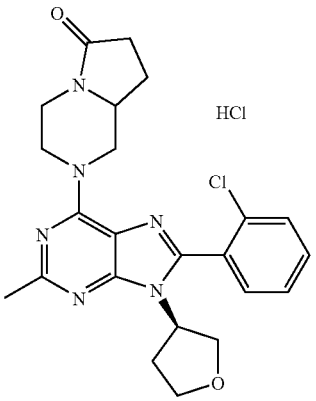 | 2-[(R)-8-(2-Chloro-phenyl)-2-methyl-9-tetrahydro-furan-3-yl-9H-purin-6-yl]-hexahydro-pyrrolo[1,2-a]pyrazin-6-one hydrochloride salt, Isomer 1[d] | MS (m/z): 453 (M + 1) |

TABLE 3-continued

| Example No. | Structure | Chemical name | Physical data |
|---|---|---|---|
| 29 | 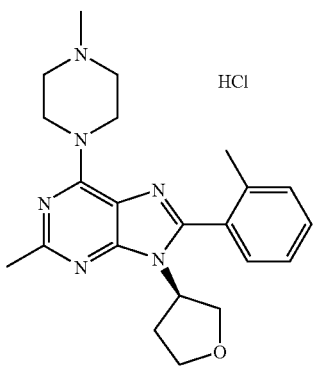 | 2-Methyl-6-(4-methyl-piperazin-1-yl)-9-(R)-tetrahydro-3-yl-8-o-tolyl-9H-purine hydrochloride salt | MS (m/z): 393 (M + 1) |
| 30 | 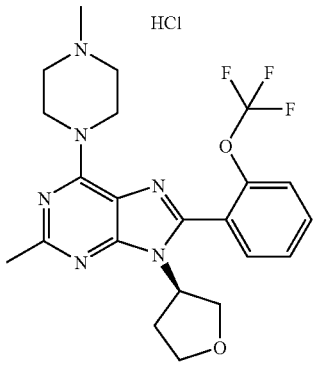 | 2-Methyl-6-(4-methyl-piperazin-1-yl)-9-(R)-tetrahydro-furan-3-yl-8-(2-trifluoromethoxy-phenyl)-9H-purine hydrochloride salt | MS (m/z): 463 (M + 1) |
| 31 | 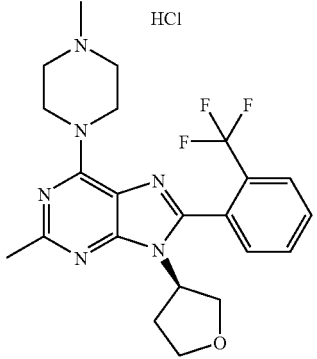 | 2-Methyl-6-(4-methyl-piperazin-1-yl)-9-(R)-tetrahydro-furan-3-yl-8-(2-trifluoromethyl-phenyl)-9H-purine hydrochloride salt | MS (m/z): 447 (M + 1) |
| 32 | 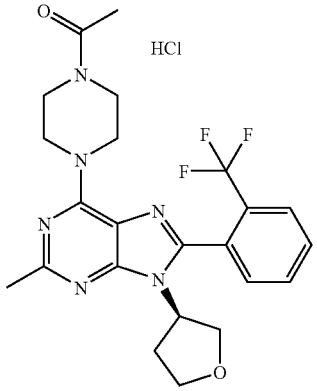 | 1-{4-[(R)-2-Methyl-9-tetrahydro-furan-3-yl-8-(2-trifluoromethyl-phenyl)-9H-purin-6-yl]-piperazin-1-yl}-ethanone hydrochloride salt | MS (m/z): 475 (M + 1) |

TABLE 3-continued

| Example No. | Structure | Chemical name | Physical data |
|---|---|---|---|
| 33 | 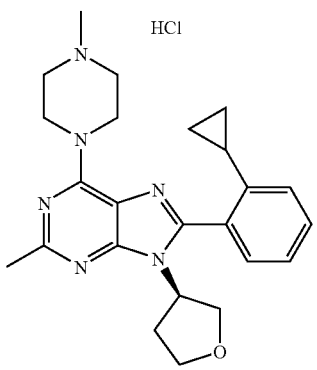 | 8-(2-Cyclopropyl-phenyl)-2-methyl-6-(4-methyl-piperazin-1-yl)-9-(R)-tetrahydro-furan-3-yl-9H-purine hydrochloride salt | MS (m/z): 419 (M + 1) |
| 34 | 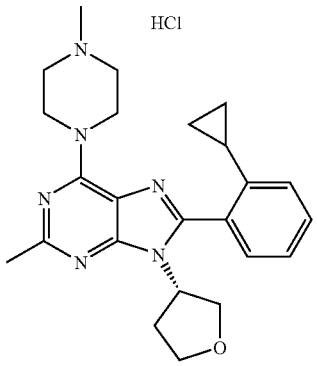 | 8-(2-Cyclopropyl-phenyl)-2-methyl-6-(4-methyl-piperazin-1-yl)-9-(S)-tetrahydro-furan-3-yl-9H-purine hydrochloride salt | MS (m/z): 419 (M + 1) |
| 35 | 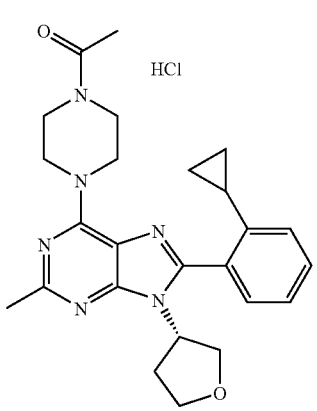 | 1-{4-[(S)-8-(2-Cyclopropyl-phenyl)-2-methyl-9-tetrahydro-furan-3-yl-9H-purin-6-yl]-piperazin-1-yl}-ethanone hydrochloride salt | MS (m/z): 447 (M + 1) |
| 36 | 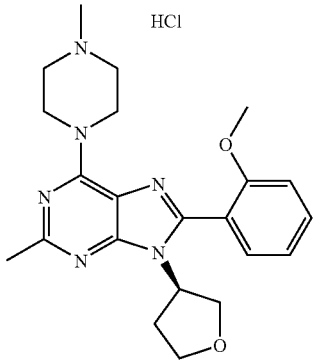 | 8-(2-Methoxy-phenyl)-2-methyl-6-(4-methyl-piperazin-1-yl)-9-(R)-tetrahydro-furan-3-yl-9H-purine hydrochloride salt | MS (m/z): 409 (M + 1) |

TABLE 3-continued

| Example No. | Structure | Chemical name | Physical data |
|---|---|---|---|
| 37 | 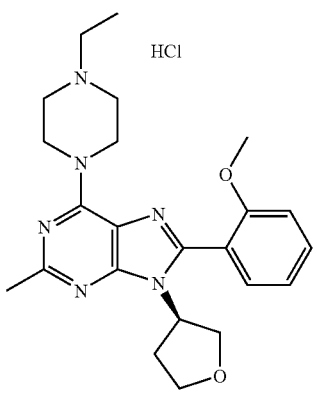 | 6-(4-Ethyl-piperazin-1-yl)-8-(2-methoxy-phenyl)-2-methyl-9-(R)-tetrahydro-furan-3-yl-9H-purine hydrochloride salt | MS (m/z): 423 (M + 1) |
| 38 | 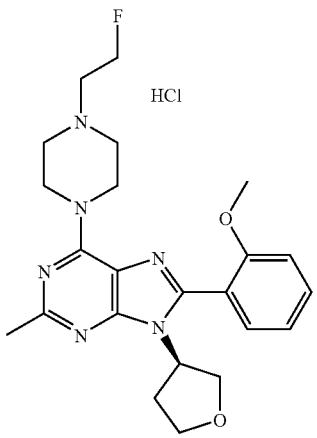 | 6-[4-(2-Fluoro-ethyl)-piperazin-1-yl]-8-(2-methoxy-phenyl)-2-methyl-9-(R)-tetrahydro-furan-3-yl-9H-purine hydrochloride salt | MS (m/z): 441 (M + 1) |
| 39 | 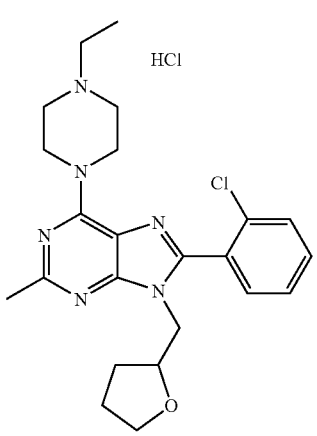 | 8-(2-Chloro-phenyl)-6-(4-ethyl-piperazin-1-yl)-2-methyl-9-(tetrahydro-furan-2-ylmethyl)-9H-purine hydrochloride salt, Isomer 1[c] | MS (m/z): 441 (M + 1) |

TABLE 3-continued

| Example No. | Structure | Chemical name | Physical data |
|---|---|---|---|
| 40 | 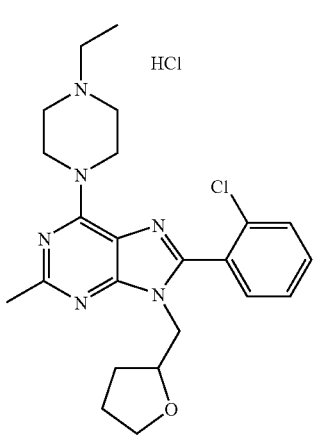 | 8-(2-Chloro-phenyl)-6-(4-ethyl-piperazin-1-yl)-2-methyl-9-(tetrahydro-furan-2-ylmethyl)-9H-purine hydrochloride salt, Isomer 2[e] | MS (m/z): 441 (M + 1) |
| 41 | 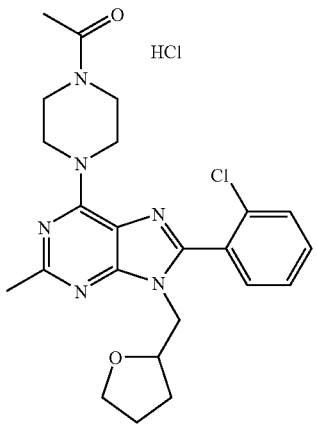 | 1-{4-[8-(2-Chloro-phenyl)-2-methyl-9-(tetrahydro-furan-2-ylmethyl)-9H-purin-6-yl]-piperazin-1-yl}-ethanone hydrochloride salt | MS (m/z): 455 (M + 1) |
| 42 | 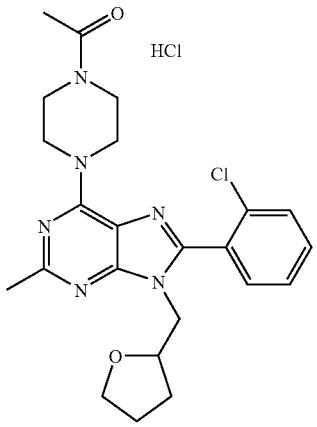 | 1-{4-[8-(2-Chloro-phenyl)-2-methyl-9-(tetrahydro-furan-2-ylmethyl)-9H-purin-6-yl]-piperazin-1-yl}-ethanone hydrochloride salt, Isomer 1[f] | MS (m/z): 455 (M + 1) |

TABLE 3-continued

| Example No. | Structure | Chemical name | Physical data |
|---|---|---|---|
| 43 | 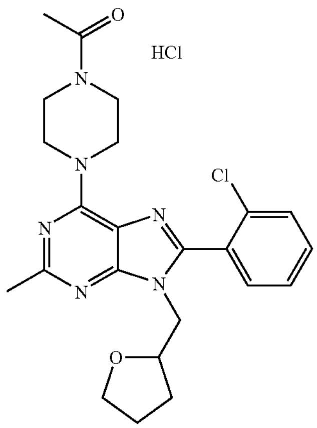 | 1-{4-[8-(2-Chloro-phenyl)-2-methyl-9-(tetrahydro-furan-2-ylmethyl)-9H-purin-6-yl]-piperazin-1-yl}-ethanone hydrochloride salt, Isomer 2[f] | MS (m/z): 455 (M + 1) |
| 44 | 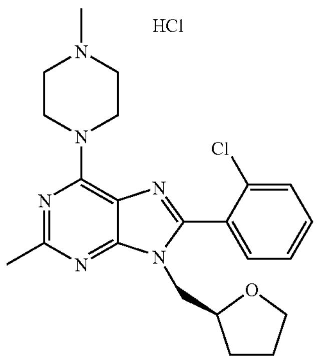 | 8-(2-Chloro-phenyl)-2-methyl-6-(4-methyl-piperazin-1-yl)-9-[(S)-1-(tetrahydro-furan-2-yl)methyl]-9H-purine hydrochloride salt | MS (m/z): 427 (M + 1) |
| 45 | 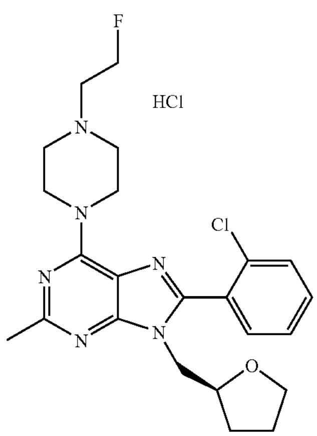 | 8-(2-Chloro-phenyl)-6-[4-(2-fluoro-ethyl)-piperazin-1-yl]-2-methyl-9-[(S)-1-(tetrahydro-furan-2-yl)methyl]-9H-purine hydrochloride salt | MS (m/z): 459 (M + 1) |
| 46 | 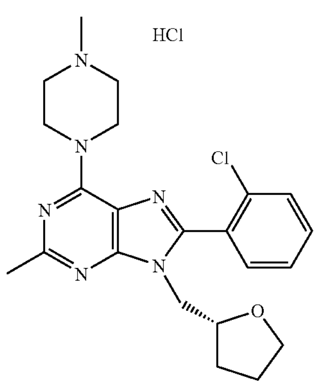 | 8-(2-Chloro-phenyl)-2-methyl-6-(4-methyl-piperazin-1-yl)-9-[(R)-1-(tetrahydro-furan-2-yl)methyl]-9H-purine hydrochloride salt | MS (m/z): 427 (M + 1) |

TABLE 3-continued

| Example No. | Structure | Chemical name | Physical data |
|---|---|---|---|
| 47 | 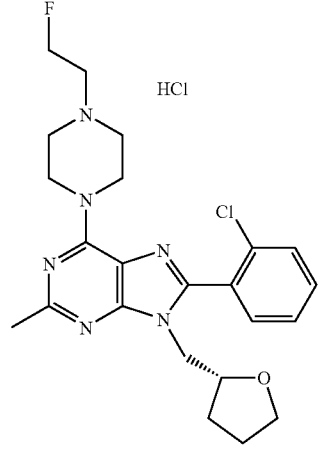 | 8-(2-Chloro-phenyl)-6-[4-(2-fluoro-ethyl)-piperazin-1-yl]-2-methyl-9-[(R)-1-(tetrahydro-furan-2-yl)methyl]-9H-purine hydrochloride salt | MS (m/z): 459 (M + 1) |
| 48 | 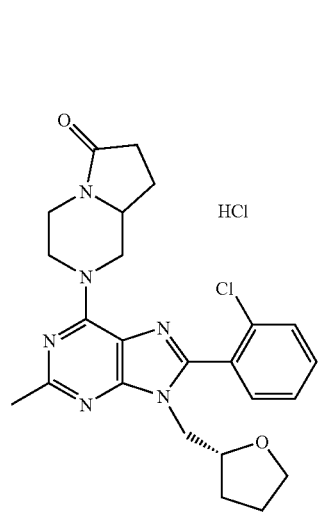 | 2-{8-(2-Chloro-phenyl)-2-methyl-9-[(R)-1-(tetrahydro-furan-2-yl)methyl]-9H-purin-6-yl}-hexahydro-pyrrolo[1,2-a]pyrazin-6-one hydrochloride salt | MS (m/z): 467 (M + 1) |
| 49 | 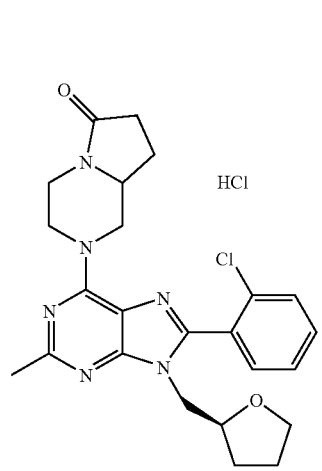 | 2-{8-(2-Chloro-phenyl)-2-methyl-9-[(S)-1-(tetrahydro-furan-2-yl)methyl]-9H-purin-6-yl}-hexahydro-pyrrolo[1,2-a]pyrazin-6-one hydrochloride salt, Isomer 1[g] | MS (m/z): 467 (M + 1) |

TABLE 3-continued

| Example No. | Structure | Chemical name | Physical data |
|---|---|---|---|
| 50 | 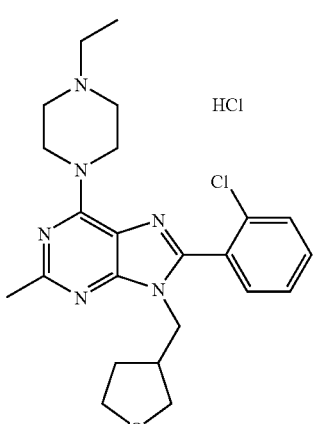 | 8-(2-Chloro-phenyl)-6-(4-ethyl-piperazin-1-yl)-2-methyl-9-(tetrahydro-furan-3-ylmethyl)-9H-purine hydrochloride salt, Isomer 1[h] | MS (m/z): 441 (M + 1) |
| 51 | 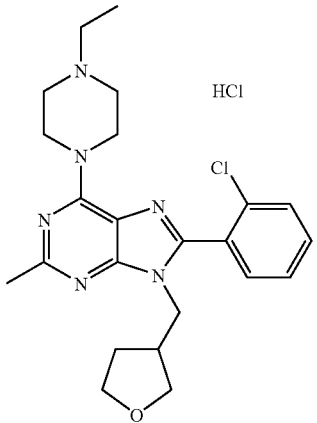 | 8-(2-Chloro-phenyl)-6-(4-ethyl-piperazin-1-yl)-2-methyl-9-(tetrahydro-furan-3-ylmethyl)-9H-purine hydrochloride salt, Isomer 2[h] | MS (m/z): 441 (M + 1) |
| 52 | 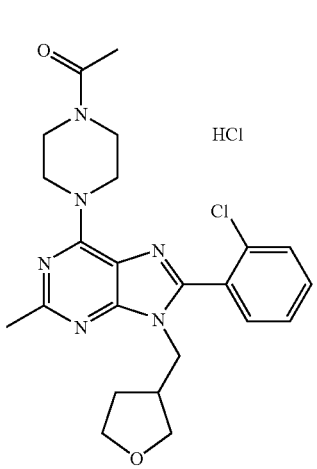 | 1-{4-[8-(2-Chloro-phenyl)-2-methyl-9-(tetrahydro-furan-3-ylmethyl)-9H-purin-6-yl]-piperazin-1-yl}-ethanone hydrochloride salt, Isomer 1[i] | MS (m/z): 455 (M + 1) |

TABLE 3-continued

| Example No. | Structure | Chemical name | Physical data |
|---|---|---|---|
| 53 | 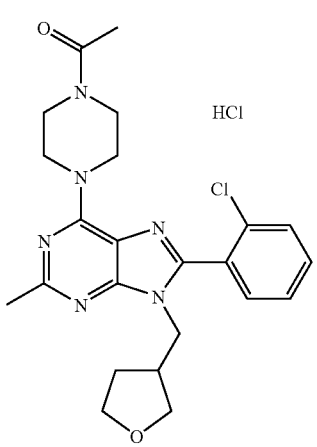 | 1-{4-[8-(2-Chloro-phenyl)-2-methyl-9-(tetrahydro-furan-3-ylmethyl)-9H-purin-6-yl]-piperazin-1-yl}-ethanone hydrochloride salt, Isomer 2$^i$ | MS (m/z): 455 (M + 1) |
| 54 | 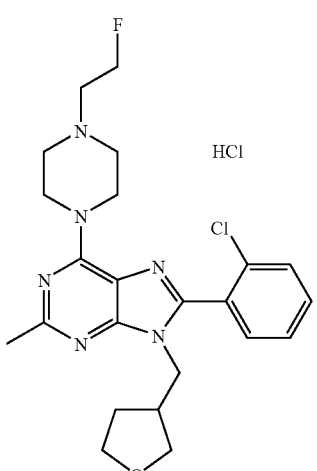 | 8-(2-Chloro-phenyl)-6-[4-(2-fluoro-ethyl)-piperazin-1-yl]-2-methyl-9-(tetrahydro-furan-3-ylmethyl)-9H-purine hydrochloride salt, Isomer 1$^j$ | MS (m/z): 459 (M + 1) |
| 55 | 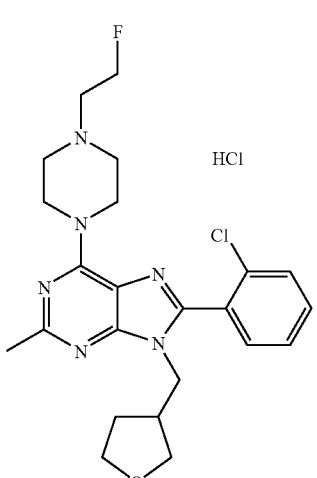 | 8-(2-Chloro-phenyl)-6-[4-(2-fluoro-ethyl)-piperazin-1-yl]-2-methyl-9-(tetrahydro-furan-3-ylmethyl)-9H-purine hydrochloride salt, Isomer 2$^j$ | MS (m/z): 459 (M + 1) |

TABLE 3-continued

| Example No. | Structure | Chemical name | Physical data |
|---|---|---|---|
| 56 | 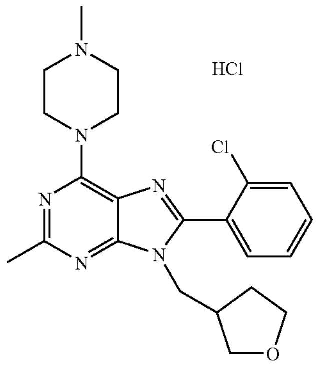 | 8-(2-Chloro-phenyl)-2-methyl-6-(4-methyl-piperazin-1-yl)-9-(tetrahydro-furan-3-ylmethyl)-9H-purine hydrochloride salt, Isomer 1[k] | MS (m/z): 427 (M + 1) |
| 57 | 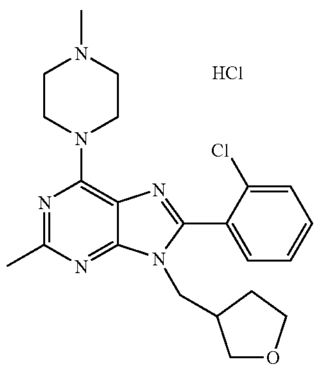 | 8-(2-Chloro-phenyl)-2-methyl-6-(4-methyl-piperazin-1-yl)-9-(tetrahydro-furan-3-ylmethyl)-9H-purine hydrochloride salt, Isomer 2[k] | MS (m/z): 427 (M + 1) |
| 58 | 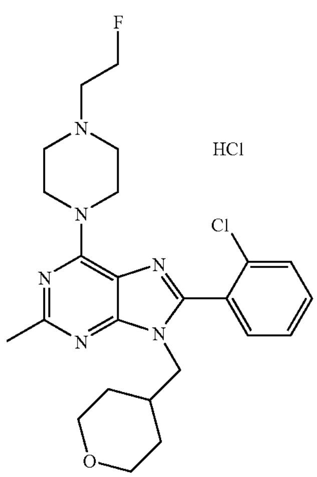 | 8-(2-Chloro-phenyl)-6-[4-(2-fluoro-ethyl)-piperazin-1-yl]-2-methyl-9-(tetrahydro-pyran-4-ylmethyl)-9H-purine hydrochloride salt | MS (m/z): 473 (M + 1) |

TABLE 3-continued

| Example No. | Structure | Chemical name | Physical data |
|---|---|---|---|
| 59 | 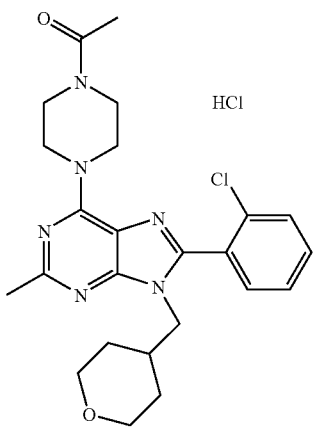 | 1-{4-[8-(2-Chloro-phenyl)-2-methyl-9-(tetrahydro-pyran-4-ylmethyl)-9H-purin-6-yl]-piperazin-1-yl}-ethanone hydrochloride salt | MS (m/z): 469 (M + 1) |
| 60 | 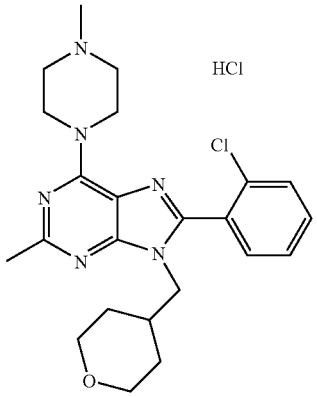 | 8-(2-Chloro-phenyl)-2-methyl-6-(4-methyl-piperazin-1-yl)-9-(tetrahydro-pyran-4-ylmethyl)-9H-purine hydrochloride | MS (m/z): 441 (M + 1) |
| 61 | 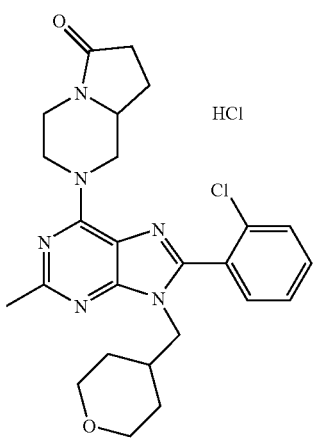 | 2-[8-(2-Chloro-phenyl)-2-methyl-9-(tetrahydro-pyran-4-ylmethyl)-9H-purin-6-yl]-hexahydro-pyrrolo[1,2-a]pyrazin-6-one hydrochloride salt, Isomer $2^I$ | MS (m/z): 481 (M + 1) |

TABLE 3-continued

| Example No. | Structure | Chemical name | Physical data |
|---|---|---|---|
| 62 | 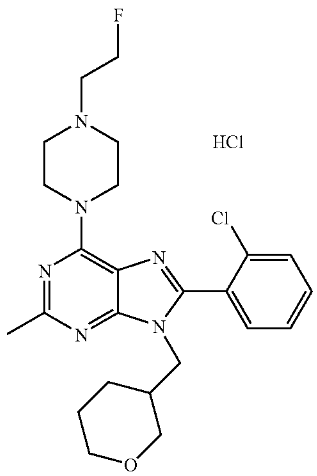 | 8-(2-Chloro-phenyl)-6-[4-(2-fluoro-ethyl)-piperazin-1-yl]-2-methyl-9-(tetrahydro-pyran-3-ylmethyl)-9H-purine-hydrochloride salt, Isomer 1'" | MS (m/z): 473 (M + 1) |
| 63 | 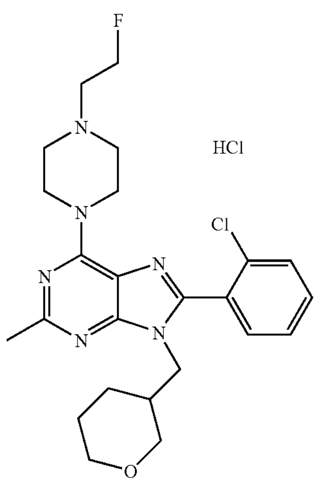 | 8-(2-Chloro-phenyl)-6-[4-(2-fluoro-ethyl)-piperazin-1-yl]-2-methyl-9-(tetrahydro-pyran-3-ylmethyl)-9H-purine hydrochloride salt, Isomer 2'" | MS (m/z): 473 (M + 1) |
| 64 | 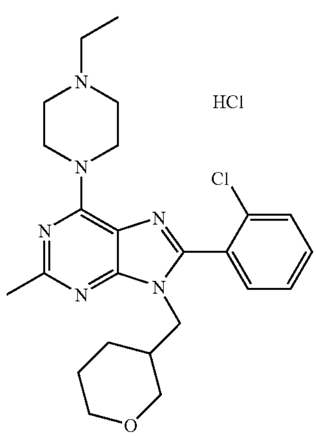 | 8-(2-Chloro-phenyl)-6-(4-ethyl-piperazin-1-yl)-2-methyl-9-(tetrahydro-pyran-3-ylmethyl)-9H-purine hydrochloride salt, Isomer 1" | MS (m/z): 455 (M + 1) |

TABLE 3-continued

| Example No. | Structure | Chemical name | Physical data |
|---|---|---|---|
| 65 | 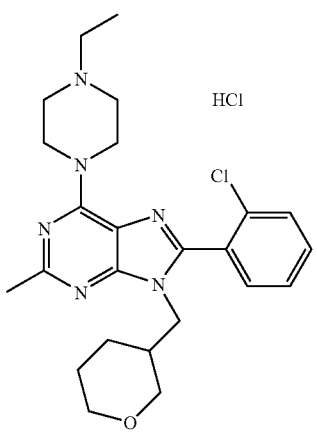 | 8-(2-Chloro-phenyl)-6-(4-ethyl-piperazin-1-yl)-2-methyl-9-(tetrahydro-pyran-3-ylmethyl)-9H-purine hydrochloride salt, Isomer 2[n] | MS (m/z): 455 (M + 1) |
| 66 | 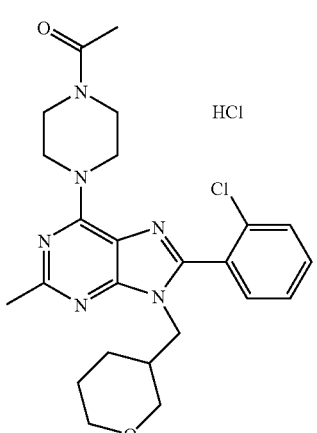 | 1-{4-[8-(2-Chloro-phenyl)-2-methyl-9-(tetrahydro-pyran-3-ylmethyl)-9H-purin-6-yl]-piperazin-1-yl}-ethanone hydrochloride salt, Isomer 1[o] | MS (m/z): 469 (M + 1) |
| 67 | 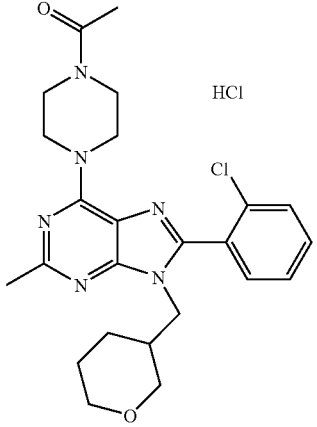 | 1-{4-[8-(2-Chloro-phenyl)-2-methyl-9-(tetrahydro-pyran-3-ylmethyl)-9H-purin-6-yl]-piperazin-1-yl}-ethanone hydrochloride salt, Isomer 2[o] | MS (m/z): 469 (M + 1) |

TABLE 3-continued

| Example No. | Structure | Chemical name | Physical data |
|---|---|---|---|
| 68 | 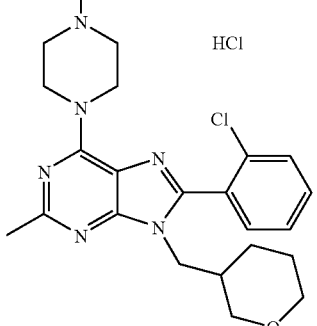 | 8-(2-Chloro-phenyl)-2-methyl-6-(4-methyl-piperazin-1-yl)-9-(tetrahydro-pyran-3-ylmethyl)-9H-purine hydrochloride salt, Isomer 1[p] | MS (m/z): 441 (M + 1) |
| 69 | 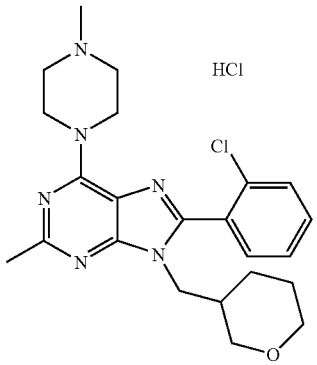 | 8-(2-Chloro-phenyl)-2-methyl-6-(4-methyl-piperazin-1-yl)-9-(tetrahydro-pyran-3-ylmethyl)-9H-purine hydrochloride salt, Isomer 2[p] | MS (m/z): 441 (M + 1) |
| 70 | 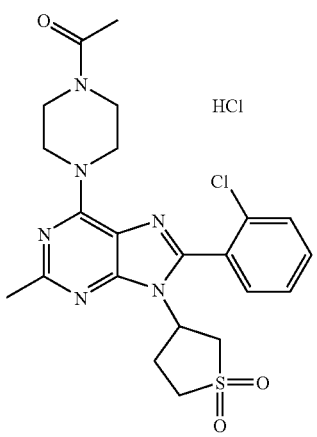 | 1-{4-[8-(2-Chloro-phenyl)-9-(1,1-dioxo-tetrahydro-1lambda*6*-thiophen-3-yl)-2-methyl-9H-purin-6-yl]-piperazin-1-yl}-ethanone hydrochloride salt, Isomer 1[q] | MS (m/z): 489 (M + 1) |
| 71 | 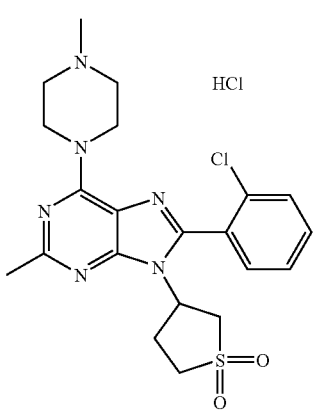 | 8-(2-Chloro-phenyl)-9-(1,1-dioxo-tetrahydro-1lambda*6*-thiophen-3-yl)-2-methyl-6-(4-methyl-piperazin-1-yl)-9H-purine hydrochloride salt, Isomer 1[r] | MS (m/z): 461 (M + 1) |

TABLE 3-continued

| Example No. | Structure | Chemical name | Physical data |
|---|---|---|---|
| 72 | 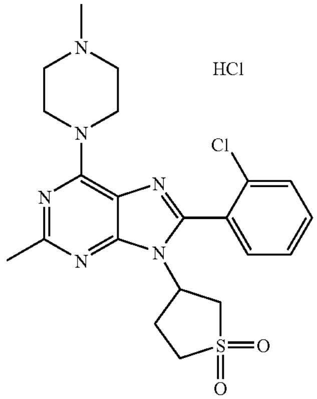 | 8-(2-Chloro-phenyl)-9-(1,1-dioxo-tetrahydro-1lambda*6*-thiophen-3-yl)-2-methyl-6-(4-methyl-piperazin-1-yl)-9H-purine hydrochloride salt, Isomer 2" | MS (m/z): 461 (M + 1) |
| 73 | 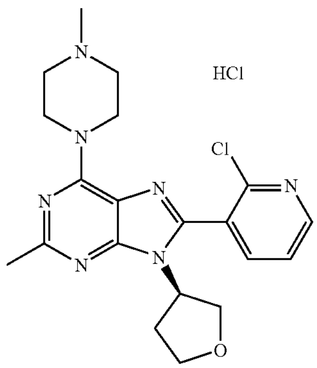 | 8-(2-Chloro-pyridin-3-yl)-2-methyl-6-(4-methyl-piperazin-1-yl)-9-(R)-tetrahydro-furan-3-yl-9H-purine hydrochloride salt | MS (m/z): 414 (M + 1) |
| 74 | 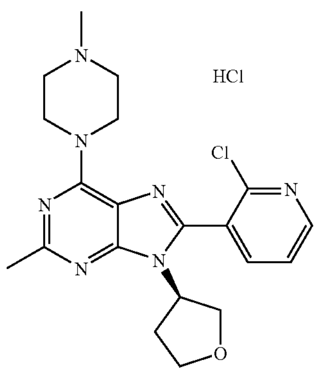 | 8-(4-Chloro-pyridin-3-yl)-2-methyl-6-(4-methyl-piperazin-1-yl)-9-(R)-tetrahydro-furan-3-yl-9H-purine hydrochloride salt | MS (m/z): 414 (M + 1) |
| 75 | 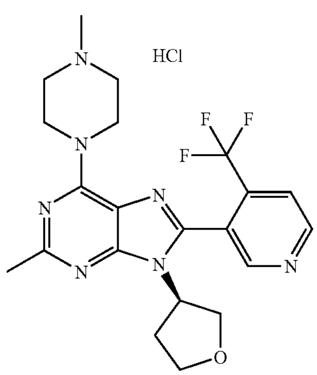 | 2-Methyl-6-(4-methyl-piperazin-1-yl)-9-(R)-tetrahydro-furan-3-yl-8-(4-trifluoromethyl-pyridin-3-yl)-9H-purine hydrochloride salt | MS (m/z): 448 (M + 1) |

TABLE 3-continued

| Example No. | Structure | Chemical name | Physical data |
|---|---|---|---|
| 76 | 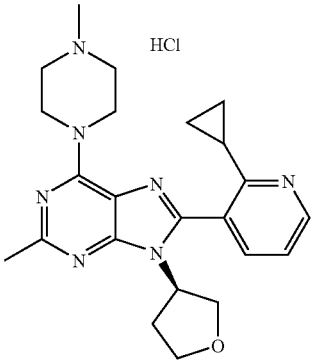 | 8-(2-Cyclopropyl-pyridin-3-yl)-2-methyl-6-(4-methyl-piperazin-1-yl)-9-(R)-tetrahydro-furan-3-yl-9H-purine hydrochloride salt | MS (m/z): 420 (M + 1) |

Superscript a-r represent chiral separation conditions: Isomer 1 is first to elute from analytical chiral column and isomer 2 is the second to elute from the chiral column.
[a]RegisPack SFC, Eluent: 10% EtOH (0.2% IPAm)/CO$_2$
[b]Chiralpak AS—H, Eluent: 100% MeOH (0.2% DMEA)
[c]Chiralpak AD—H, Eluent 40:60 IPA:heptane (0.2% DMEA)
[d]Chiralpak AD—H SFC, Eluent: 20% IPA (0.2% IPAm)/CO$_2$
[e]Chiralpak AD—H SFC, Eluent: 7% MeOH (0.2% IPAm)/CO$_2$
[f]Chiralpak AS—H, Eluent: 100% EtOH
[g]Chiralpak AD—H, Eluent: 30:70 IPA:heptane (0.2% DMEA)
[h]Chiralpak AD—H SFC, Eluent: 10% EtOH (0.2% IPAm)/CO$_2$
[i]Chiralcel OJ—H SFC, Eluent: 10% MeOH (0.2% IPAm)/CO$_2$
[j]Chiralpak AD—H SFC, Eluent: 10% EtOH (0.2% IPAm)/CO$_2$
[k]Chiralpak AD—H, Eluent: 15.85 IPA:heptane (0.2DMEA)
[l]Chiralpak AD—HSFC, Eluent: 20%MeOH (0.2% IPAm)/CO$_2$
[m]Chiralpak AD—H SFC, Eluent: 10% EtOH (0.2% IPAm)CO$_2$
[n]Chiralpak AD—HSFC, Eluent: 10% EtOH (0.2% IPAm)CO$_2$
[o]Chiralpak AS—H SFC, Eluent: 10% MeOH (0.2% IPAm)/CO$_2$
[p]Chiralpak AD—H, Eluent: 5:95 EtOH:heptane (0.2% DMEA)
[q]Chiralpak AS—H, Eluent: 100% MeOH (0.2% DMEA)
[r]Chiralpak AS—H, Eluent: 100% MeOH (0.2% DMEA)

EXAMPLE 77

8-(4-Methoxy-2-methyl-phenyl)-2-methyl-6-(4-methyl-piperazin-1-yl)-9-(R)-tetrahydro-furan-3-yl-9H-purine

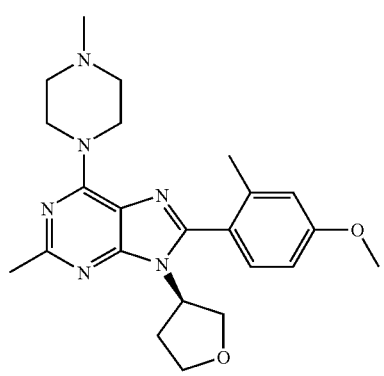

Dissolve 6-chloro-2-methyl-N*4*-(R)-tetrahydro-furan-3-yl-pyrimidine-4,5-diamine (0.100 g, 0.402 mmol), 4-methoxy-2-methylbenzaldehyde (0.091 g, 0.603 mmol), N-methylpiperazine (0.044 g, 0.443 mmol) and nitrobenzene (0.050 g, 0.402 mmol) in methoxybenzene (1.2 mL) and heat to 140° C. for 2 days. Next, stir at room temperature for 3 days. Next, concentrate under reduced pressure and partition between aqueous 2N HCl and dichloromethane, wash with dichloromethane. Basify aqueous phase to pH 12 and extract with dichloromethane. Load organics onto 5 g SCX-2 column, wash with methanol then elute product with 2N ammonia in methanol. Purify by prep high-pressure liquid chromatography and lyophilize from water/acetonitrile to afford the title compound as the freebase. MS (m/z): 423 (M+1).

EXAMPLE 78

2-[2-Methyl-6-(4-methyl-piperazin-1-yl)-9-(tetrahydro-pyran-4-yl)-9H-purin-8-yl]-benzonitrile hydrochloride salt

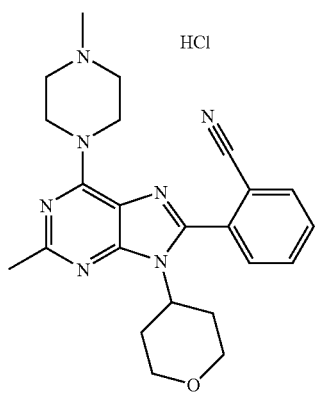

Step 1:

Heat a solution of 8-(2-bromophenyl)-6-chloro-2-methyl-9-(tetrahydro-2H-pyran-4-yl)-9H-purine (0.0023 mol, 1.0 g), 1-methyl piperazine (0.0025 mol, 0.25 g, 1.1 equiv.) and triethylamine (0.0025 mol, 0.25 g, 1.1 equiv.) in ethanol (10.0 mL) at 90° C. for 16 h. Concentrate the reaction mixture under reduce pressure. Dissolve the residue in dry dichloromethane and wash with saturated sodium bicarbonate solution, water, and brine. Dry the organic layer over anhydrous sodium sulfate, filter, and concentrate to give the residue. Purify the residue by silica gel chromatography eluting with dichloromethane:methanol 97:3 to give 8-(2-Bromo-phenyl)-2-methyl-6-(4-methyl-piperazin-1-yl)-9-(tetrahydro-pyran-4-yl)-9H-purine (0.71 g). Used as such for the next step.

Step 2:

Charge a microwave reaction vessel with 8-(2-Bromo-phenyl)-2-methyl-6-(4-methyl-piperazin-1-yl)-9-(tetrahydro-pyran-4-yl)-9H-purine (0.0015 mol, 0.7 g), zinc cyanide (0.0022 mol, 0.256 g, 1.5 equiv.), and dry N,N-dimethylformamide (5.0 mL). Degas three times with nitrogen. Add Pd(PPh$_3$)$_4$ (0.0001 mol, 0.17 g, 0.1 equiv.) and degas again three times with nitrogen. Seal the reaction vessel and irradiate at 150° C. for 1 hour in microwave. Cool the reaction mixture to room temperature, quench the reaction mixture with water and extract with ethyl acetate. Wash the organic layer with brine, dry over anhydrous sodium sulfate, filter, and concentrate under reduced pressure to give a residue. Purify the residue on silica gel column eluting with dichloromethane:methanol 99:1 to give the freebase. Add HCl (2M solution in diethyl ether) (0.026 g, 0.0007 mol, 1.0 equiv.) to the mixture of 2-(2-methyl-6-(4-methylpiperazin-1-yl)-9-(tetrahydro-2H-pyran-4-yl)-9H-purin-8-yl)benzonitrile (0.3 g, 0.0007 mol) in diethyl ether (5 mL) at 0° C. and stir for 2 hours at room temperature. Filter the precipitate, wash with diethyl ether, and dry in a vacuum to give the title compound. MS (m/z): 418.29 (M+1).

Examples 79-80 in Table 4 may be prepared essentially by the same procedure over two steps as example 78 using the appropriately substituted purine according to Scheme E.

TABLE 4

| Ex. No. | Structure | Chemical name | Physical data |
|---|---|---|---|
| 79 | 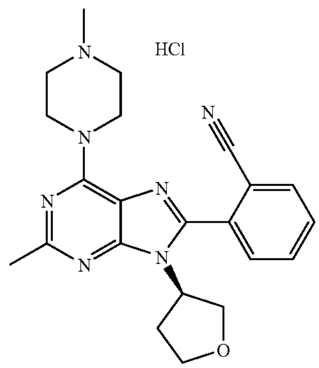 | 2-[(R)-2-Methyl-6-(4-methyl-piperazin-1-yl)-9-tetrahydro-furan-3-yl-9H-purin-8-yl]-benzonitrile hydrochloride salt | MS (m/z): 404 (M + 1) |
| 80 | 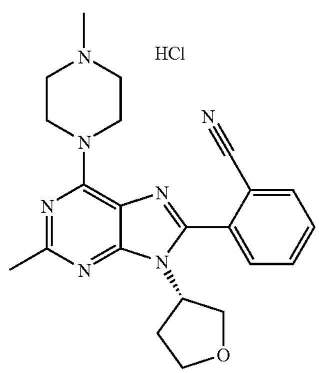 | 2-[(S)-2-Methyl-6-(4-methyl-piperazin-1-yl)-9-tetrahydro-furan-3-yl-9H-purin-8-yl]-benzonitrile hydrochloride salt | MS (m/z): 404 (M + 1) |

EXAMPLE 81

2-Methyl-6-(4-methyl-piperazin-1-yl)-9-(tetrahydro-pyran-4-yl)-8-o-tolyl-9H-hydrochloride salt

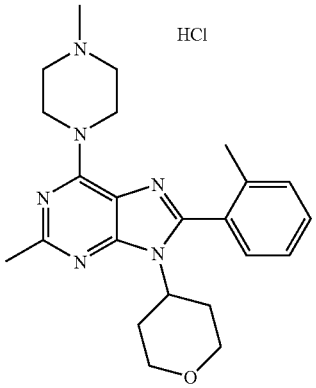

To a solution of 6-Chloro-2-methyl-N*4*-(tetrahydro-pyran-4-yl)-pyrimidine-4,5-diamine (1 g, 4.12 mmoles) in dimethyl sulfoxide (5 mL) is added o-tolualdehyde 4.12 mmol), N-methylpiperazine (4.12 mmol) followed by acetic acid (9.89 mmoles, 566.635 µL). This reaction is heated to 90° C. open to the atmosphere for 8 hours. Material is charged onto a pre-conditioned SCX column and eluted with 7N ammonia in methanol, solvent evaporated and crude is purified reverse phase chromatography. To the material is added 1 equivalent of HCl 4M in 1,4-dioxane. The excess solvent is evaporated to give the title compound. MS (m/z): 407 (M+1).

Examples 82-83 in Table 5 may be prepared essentially as described in Example 81 using the appropriate pyrimidine, aldehyde, and piperazine according to Scheme F.

TABLE 5

| Ex. No. | Structure | Chemical name | Physical data |
|---|---|---|---|
| 82 | 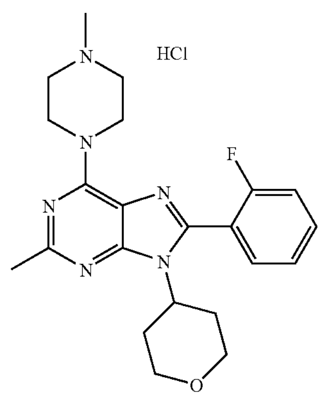 | 8-(2-Fluoro-phenyl)-2-methyl-6-(4-methyl-piperazin-1-yl)-9-(tetrahydro-pyran-4-yl)-9H-purine hydrochloride salt | MS (m/z): 411 (M + 1) |

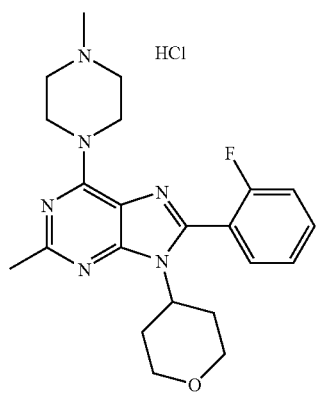

| 83 | | 8-(2-Ethyl-phenyl)-2-methyl-6-(4-methyl-piperazin-1-yl)-9-(tetrahydro-pyran-4-yl)-9H-purine hydrochloride salt | MS (m/z): 421 (M + 1) |

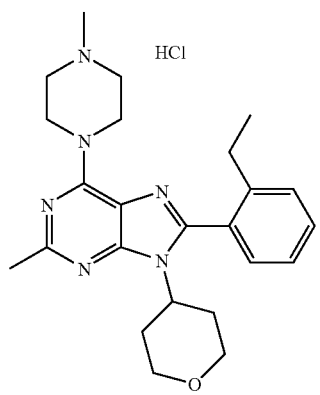

EXAMPLE 84

3-[8-(2-Chloro-phenyl)-6-(4-ethyl-piperazin-1-yl)-2-methyl-purin-9-yl]-azetidine-1-carboxylic acid methylester

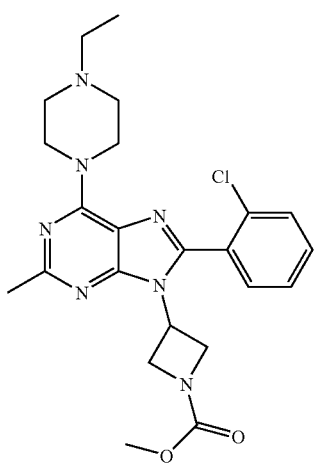

Step 1:

Heat a solution of tert-butyl 3-(6-chloro-8-(2-chlorophenyl)-2-methyl-9H-purin-9-yl)azetidine-1-carboxylate (0.012 mol, 5.5 g), N-ethyl piperazine (0.013 mol, 1.59 g, 1.1 equiv.), and triethylamine (0.013 mol, 1.41 g, 1.1 equiv.) in ethanol (25.0 mL) at 90° C. for 16 hours. Concentrate the reaction mixture under reduced pressure. Dissolve the residue in dry dichloromethane. Wash with saturated sodium bicarbonate solution, water, and brine. Dry the organic layer over anhydrous sodium sulfate, filter, and concentrate under reduced pressure to give the residue. Purify the residue by silica gel chromatography eluting with dichloromethane:methanol 98:2 to give tert-butyl 3-(8-(2-chlorophenyl)-6-(4-ethylpiperazin-1-yl)-2-methyl-9H-purin-9-yl)azetidine-1-carboxylate (3.0 g). MS (m/z): 512.31 (M+1).

Step 2:

Add trifluoroacetic acid (15 mL) to a solution of tert-butyl 3-(8-(2-chlorophenyl)-6-(4-ethylpiperazin-1-yl)-2-methyl-9H-purin-9-yl)azetidine-1-carboxylate (0.005 mol, 3.0 g) in dichloromethane (15 mL) at 0° C. and stir for 2 hours at room temperature. Quench the reaction mixture with saturated sodium bicarbonate solution and extract with dichloromethane. Dry the organic layer over anhydrous sodium sulfate, filter, and concentrate under reduced pressure to give 9-(azetidin-3-yl)-8-(2-chlorophenyl)-6-(4-ethylpiperazin-1-yl)-2-methyl-9H-purine (2.4 g). MS (m/z): 412.22 (M+1).

Step 3:

Add methyl chloroformate (0.0024 mol, 0.22 g, 2.5 equiv.) to a solution of 9-(azetidin-3-yl)-8-(2-chlorophenyl)-6-(4-ethylpiperazin-1-yl)-2-methyl-9H-purine (0.0009 mol, 0.4 g) and pyridine (2 mL) in dry dichloromethane (2 mL) at 0° C. and stir for 2 hours at room temperature. Quench the reaction mixture with saturated sodium bicarbonate solution and then extract with dichloromethane. Dry the organic layer over anhydrous sodium sulfate, filter and concentrate under reduced pressure to give the residue. Purify the residue by silica gel chromatography eluting with dichloromethane: methanol 98:2 to give the title compound as the freebase (0.155 g). MS (m/z): 470.63 (M+1).

EXAMPLE 85

8-(2-Chloro-phenyl)-6-(4-methyl-piperazin-1-yl)-9-(tetrahydro-pyran-4-ylmethyl)-9H-purine hydrochloride salt

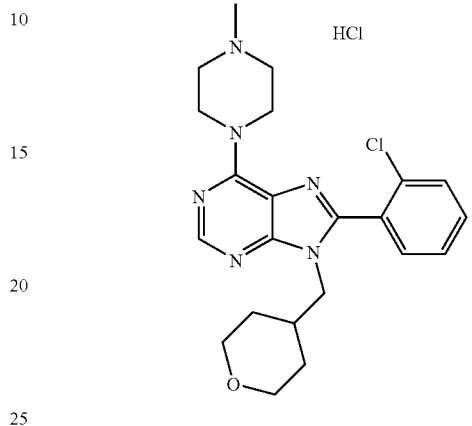

Step 1:

Charge a microwave reaction vial with 4,6-dichloro-pyrimidin-5-ylamine (12.20 mmoles, 2.00 g), isopropyl alcohol (5 mL), C-(tetrahydro-pyran-4-yl)-methylamine (14.63 mmoles, 1.69 g), and N,N-diisopropylethylamine (15.85 mmoles, 2.76 mL). Irradiate with stirring at 140° C. for 2 hours with high absorbance mode in the microwave. Solvent is evaporated and residue triturated with dichloromethane to afford 6-Chloro-N*4*-(tetrahydro-pyran-4-ylmethyl)-pyrimidine-4,5-diamine Step 2:

Prepare 6-Chloro-8-(2-chloro-phenyl)-9-(tetrahydro-pyran-4-ylmethyl)-9H-purine is using 6-Chloro-N*4*-(tetrahydro-pyran-4-ylmethyl)-pyrimidine-4,5-diamine according to general procedure 2-1.

Step 3:

Displace 6-Chloro-8-(2-chloro-phenyl)-9-(tetrahydro-pyran-4-ylmethyl)-9H-purine with N-methylpiperazine and prepare hydrochloride salt using the same procedure as example 1 to give the title compound. MS (m/z): 427 (M+1)

EXAMPLE 86

8-(2-Chloro-phenyl)-6-(4-methyl-piperazin-1-yl)-9-(R)-tetrahydro-furan-3-yl-2-trifluoromethyl-9H-purine hydrochloride salt

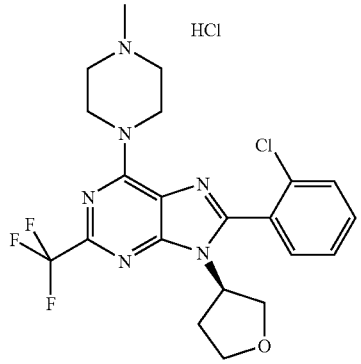

Step 1:

Charge a microwave reaction vessel with 4,6-dichloro-2-trifluoromethyl-pyrimidin-5-ylamine (4.31 mmoles, 1.00 g), isopropyl alcohol (3 mL), (R)-(tetrahydro-furan-3-yl)amine (5.17 mmoles, 639.24 mg), diisopropylethylamine (12.93 mmoles, 2.26 mL). Irradiate with stirring at 140° C. for 2 hours using the high absorbance mode. Concentrate under reduced pressure, dissolve in dichloromethane, and wash with water (2×150 mL). The organic layer is dried over magnesium sulfate and evaporated to afford a brown oil. Purify by silica gel chromatography eluting with hexanes:ethyl acetate 0-100% to afford 6-Chloro-N*4*-(R)-tetrahydro-furan-3-yl-2-trifluoromethyl-pyrimidine-4,5-diamine Step 2:

Treat 6-chloro-N*4*-(R)-tetrahydro-furan-3-yl-2-trifluoromethyl-pyrimidine-4,5-diamine (2.67 mmoles, 0.756 g) and 2-chloro-benzaldehyde (2.94 mmoles, 331.39 μL) in anhydrous 1,4-dioxane (10 mL) with 15% ferric chloride on silica (8.56 mmoles, 1.39 g) and heat at 100° C. overnight. Filter through diatomaceous earth and wash with ethyl acetate. Evaporate filtrate to afford 6-Chloro-8-(2-chloro-phenyl)-9-(R)-tetrahydro-furan-3-yl-2-trifluoromethyl-9H-purine.

Step 3:

Displace 6-Chloro-8-(2-chloro-phenyl)-9-(R)-tetrahydro-furan-3-yl-2-trifluoromethyl-9H-purine with N-methylpiperazine and prepare hydrochloride salt using the same procedure as example 1 to give title compound. MS (m/z): 467 (M+1).

EXAMPLE 87

8-(2-Chloro-phenyl)-6-(4-ethyl-piperazin-1-yl)-2-methyl-9-(tetrahydro-pyran-4-ylmethyl)-9H-purine hydrochloride salt.

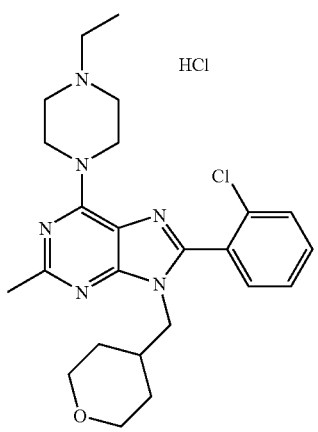

Step 1:

In a 1 L rbf fitted with reflux condenser, nitrogen inlet and stirring bar, dissolve 5-amino-4,6-dichloro-2-methylpyrimidine (25 g, 140 mmol), 4-aminomethyltetrahydropyran hydrochloride (36.2 g, 239 mmol), triethylamine (57 mL, 407.3 mmol) in isopropyl alcohol (280 mL) and heat to reflux. After 42 hours allow to cool to room temperature. Remove the solvent under reduced pressure and dissolve the resulting residue in dichloromethane (300 mL). Wash the organic layer with water (2×150 mL) and brine (150 mL), dry over anhydrous sodium sulfate, filter and evaporate to afford 6-chloro-2-methyl-N-4-(tetrahydro-pyran-4-ylmethyl)-pyrimidine-4,5-diamine (38 g). MS (m/z): 257/259 (M+1).

Step 2:

In a 3 necked 1 L rbf, fitted with thermometer, condenser and a fritted air inlet dissolve 6-chloro-2-methyl-N-4-(tetrahydro-pyran-4-ylmethyl)-pyrimidine-4,5-diamine (37.6 g, 146.4 mmol) and copper(II) trifluoromethanesulfonate (26.5 g, 73.2 mmol) in dimethylformamide (585 mL) at room temperature. Then add triethylamine (41 mL, 293 mmol), N-ethylpiperazine (20.6 mL, 161.1 mmol) and 2-chlorobenzaldehyde (24.7 mL, 219.7 mmol) and heat the mixture to 100° C. with stirring and air sparging.

After 5.5 hours, stop heating and cool to room temperature. Dilute with ethyl acetate (1 L) and wash with saturated aqueous sodium hydrogen carbonate (1×200 mL) and ammonium hydroxide (1×200 mL). Dry the organic layer over anhydrous sodium sulfate, filter, and evaporate to afford a brown oil and purify by silica gel chromatography (4% methanol in dichloromethane) to afford 8-(2-Chloro-phenyl)-6-(4-ethyl-piperazin-1-yl)-2-methyl-9-(tetrahydro-pyran-4-ylmethyl)-9H-purine (17.6 g). MS (m/z): 455/457 (M+1).

Step 3:

Stir 8-(2-Chloro-phenyl)-6-(4-ethyl-piperazin-1-yl)-2-methyl-9-(tetrahydro-pyran-4-ylmethyl)-9H-purine (5.23 g, 11.5 mmol) in diethyl ether (45 mL) and add hydrogen chloride (4N in 1,4-dioxane, 2.9 mL, 11.5 mmol) at room temperature. After 2 hours collect the solid obtained by filtration and wash with diethyl ether. Vacuum dry to afford the title compound (5.4 g) MS (m/z): 455/457 (M+1−HCl).

EXAMPLE 88

8-(2-Chloro-phenyl)-2-methyl-6-(4-methyl-piperazin-1-yl)-9-(R)-tetrahydro-furan-3-yl-9H-purine hydrochloride salt

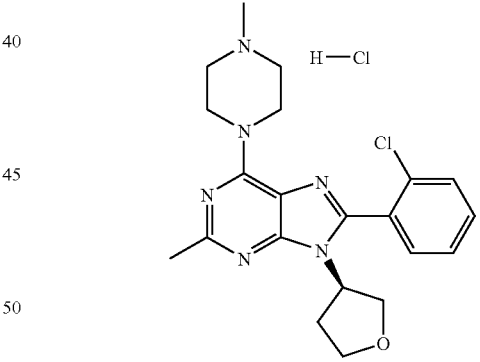

Step 1:

In a 1 L rbf fitted with reflux condenser, stirring bar and nitrogen inlet, combine 5-amino-4,6-dichloro-2-methylpyrimidine (20 g, 112.3 mmol), (R)-(tetrahydro-furan-3-yl)amine hydrochloride (20.8 g, 168.5 mmol), triethylamine (45 mL, 325.81 mmol) and isopropyl alcohol (225 mL) and heat to reflux with magnetic stirring. After 4 days stop heating and allow to cool to room temperature. Remove the solvent under reduced pressure and dissolve the resulting residue in dichloromethane (300 mL) and wash with water (2×150 mL) and brine (150 mL). Dry the organic layer over anhydrous sodium sulfate, filter and evaporate to afford 6-chloro-2-methyl-N*4*-(R)-tetrahydro-furan-3-yl-pyrimidine-4,5-diamine (23.1 g). MS (m/z):229/231 (M+1)

Step 2:

Dissolve 6-chloro-2-methyl-N*4*-(R)-tetrahydro-furan-3-yl-pyrimidine-4,5-diamine (23.1 g, 101 mmol), 2-chlorobenzaldehyde (17.0 mL. 151.5 mmol), N-methylpiperizine (12.3 mL, 111.12 mmol) and nitrobenzene (10.3 mL, 101.01 mmol) in Methoxybenzene (300 mL) and heat to 130° C. (internal temp) open to air. After 36 hours the mixture was cooled to room temperature and pour onto a pad of SCX-2 resin (80 g) and elute with methanol (500 mL) followed by 3.5N ammonia in methanol (500 mL). Remove the solvent from the ammonia in methanol fractions to afford a brown oil and purify by silica gel chromatography eluting with dichloromethane:methanol 3-20% to afford 8-(2-Chloro-phenyl)-2-methyl-6-(4-methyl-piperazin-1-yl)-9-(R)-tetrahydro-furan-3-yl-9H-purine as a dark oil (10.1 g). MS (m/z): 413/415 (M+1).

Step 3:

Dissolve 8-(2-Chloro-phenyl)-2-methyl-6-(4-methyl-piperazin-1-yl)-9-(R)-tetrahydro-furan-3-yl-9H-purine (8.62 g, 20.9 mmol) in diethyl ether (105 mL) and treat with hydrogen chloride (4 N in dioxane, 5.2 mL, 20.88 mmol). Stir the mixture for 15 hours and collect the solids that are formed by filtration. This gave a free-flowing yellow solid. The majority of this material was therefore transferred to a round bottomed flask and placed under vacuum to afford the title compound (7.33 g). MS (m/z): 413/415 (M+1−HCl), $[\alpha]_D^{20}=+27°$ (c=0.256 in dichloromethane).

EXAMPLE 89

8-(2-Chloro-phenyl)-2-methyl-6-(4-methyl-piperazin-1-yl)-9-(tetrahydro-pyran-4-yl)-9H-purine phosphate salt

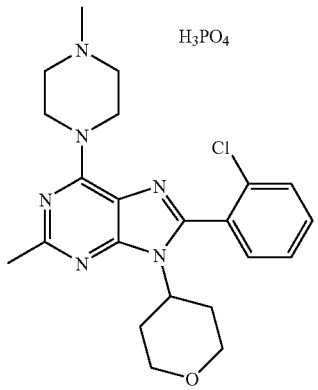

Step 1:

In a 300 mL glass pressure reactor, combine 5-amino-4,6-dichloro-2-methylpyrimidine (20.0 g, 97%, 109.0 mmol), 4-aminotetrahydropyran hydrochloride (21.0 g, 152.6 mmol), di-isopropylethylamine (57.0 mL, 326.9 mmol) and isopropyl alcohol (100 mL). Seal the pressure vessel tightly, start stirring, and adjust the set-point for heat control to 100° C. Stir the mixture at 100° C. for 24 hours. Cool the reactor contents to 60° C., vent the vessel of pressure, and add 4-aminotetrahydropyran hydrochloride (2.25 g, 16.3 mmol). Reseal the vessel, heat the contents to an internal temperature of 100° C., and stir for an additional 24 hours. Cool the reaction mixture to ambient temperature, vent the reactor of pressure, and transfer the contents to a recovery flask. Concentrate the mixture under reduced pressure to approximately ⅓ of its original volume. Add water (200 mL) and ethyl acetate (200 mL) and transfer the resulting mixture to a separatory funnel Separate the layers, re-extract the aqueous layer with ethyl acetate (100 mL) and combine all organics. Wash with water (2×100 mL) and brine (100 mL), then dry the organic layer over anhydrous sodium sulfate. Concentrate under reduced pressure to afford 6-chloro-2-methyl-N*4*-(tetrahydro-2H-pyran-4-yl)-pyrimidine-4,5-diamine as an off-white solid (25.0 g). MS (m/z): 243/245 (M+1).

Step 2:

Dissolve 6-chloro-2-methyl-N*4*-(tetrahydro-2H-pyran-4-yl)-pyrimidine-4,5-diamine (24.4 g, 100.4 mmol) in dimethylacetamide (175 mL) in a 500 mL 3-necked flask under a nitrogen atmosphere. Cool the resulting solution to 0-5° C. Via addition funnel, add 2-chlorobenzoyl chloride (15.5 mL, 122.4 mmol) over 20 minutes, maintaining the internal temperature below 10° C. Rinse the addition funnel with dimethylacetamide (1.0 mL). Allow the resulting mixture to stir overnight while self-warming to ambient temperature. Charge ice cold de-ionized water (250 mL) to a second 500 mL flask and then transfer the reaction mixture into the cold water over 20 minutes. Stir the resulting slurry for 2 hours. Filter the solids, wash with cold water (120 mL)) and vacuum dry overnight at 50° C. to afford 2-chloro-N-(4-chloro-2-methyl-6-(tetrahydro-2H-pyran-4-ylamino)-pyrimidin-5-yl)benzamide as an off-white solid (33.1 g). MS (m/z): 381/382 (M+1).

Step 3:

Combine 2-chloro-N-(4-chloro-2-methyl-6-(tetrahydro-2H-pyran-4-ylamino)-pyrimidin-5-yl) benzamide (45.0 g, 118.0 mmol), 1-methylpiperazine (23.0 mL, 207.0 mmol), di-isopropylethylamine (23.0 mL, 131.9 mmol) and isopropyl alcohol (225 mL) in a 1 L Parr reactor. Seal the reactor, start stirring, and adjust the set-point for heat control to 160° C. After the internal temperature reaches 160° C., stir the mixture for 24 hours. Cool the reactor contents to 60° C., vent the vessel of pressure, and transfer the contents to a 2 L flask equipped with overhead stirring apparatus. Rinse out reactor flask with isopropyl alcohol (25.0 mL) and combine the rinse with main solution. Add cold, de-ionized water (780 mL) to the mixture over 30 minutes and stir the resulting precipitate for 30 minutes. Filter the mixture, wash the solids with de-ionized water (2×270 mL) and pull dry on the funnel Further dry the product overnight at 45° C. to afford the 8-(2-Chloro-phenyl)-2-methyl-6-(4-methyl-piperazin-1-yl)-9-(tetrahydro pyran-4-yl)-9H-purine as an off-white solid (44.8 g) MS (m/z): 427/429 (M+1).

Step 4:

Combine 8-(2-Chloro-phenyl)-2-methyl-6-(4-methyl-piperazin-1-yl)-9-(tetrahydro pyran-4-yl)-9H-purine (3.0 g, 7.1 mmol) and absolute ethanol (24 mL) in a 50 mL 3-necked flask set up for reflux. Heat the resulting suspension to 70° C. and add 85% phosphoric acid (0.49 mL, 7.2 mmol) in absolute ethanol (6.0 mL) over 25 minutes. Stir the mixture at 70° C. for 45 minutes, cool slowly to ambient temperature and stir for an additional 2 hours. Filter the mixture, rinse the product cake with absolute ethanol (6 mL) and pull dry. Further dry the product overnight at 55° C. to afford the title compound as a white crystalline solid (3.6 g). MS (m/z): 427/429 (M+1).

$CB_1$ and $CB_2$ In Vitro Functional Assays

Exemplified compounds are tested in agonist mode using a SPA based GTP-γ-$^{35}$S binding assay. All assay components are prepared in assay buffer made up of 20 mM HEPES, 100 mM NaCl, 5 mM $MgCl_2$, (pH 7.4 at room temperature). Semi-log compound dilutions are done in assay buffer containing BSA (final 0.125%). GTP-γ$^{35}$-S binding is measured in a 96 well format using a whole membrane capture technique for the CB$_1$ assay and modifications of an antibody capture technique previously described (DeLapp et al. *J Pharmacol Exp Ther* 289:946-955, 1999) for the CB$_2$ assay. All incubations are done at room temperature.

CB$_1$:

hCB$_1$-CHO membranes, GDP (1 uM final), and saponin (10 ug/mL final) are added to assay buffer and homogenized. Diluted compounds, GTP-γ-$^{35}$S (500 nM final) and membranes are added to the assay plate and incubated for 30 minutes. Then 1 mg/well Wheatgerm Agglutinin SPA bead is added, and the plates are sealed, vortexed, and incubated for an additional hour. Plates are then centrifuged at 700×g for 10 minutes and counted for 1 minute per well using a scintillation counter.

CB$_2$-Sf9:

hCB$_2$-Sf9 membranes and GDP (1 uM final) are added to assay buffer and homogenized. Diluted compounds and membranes are added to the assay plate and pre-incubated for 15 minutes. This is followed by addition of GTP-γ-$^{35}$S (500 nM final) and another 35 minute incubation. Next a mixture containing Nonidet® P40 detergent (0.2% final), anti-Gi antibody (final dilution of 1:362), and 1.25 mg anti-rabbit antibody scintillation proximity assay beads is added. The plates are then sealed, vortexed, and incubated for an additional 2 hours before centrifuging and counting as for CB$_1$.

To analyze data, first subtract background from all wells. Determine percent agonist efficacy by normalizing agonist/inverse agonist dose response data to a full agonist (methanandamide) response. Analyze the data using a 4-parameter logistic reduced fit with Activity Base and XLFit3.

All of the exemplified compounds were tested essentially as described above and each were found to have a relative EC50 value for CB$_2$ of ≦100 nM. Example 61 has a relative EC50 value for CB$_2$ of 18 nM and for CB$_1$ of 1950 nM.

Thus, the compounds of the present invention show CB$_2$ in vitro activity. Further, the compounds of the present invention show selectivity for CB$_2$ over CB$_1$ and so provide limited potential for centrally mediated side effects.

Displacement of 3H-CP55940 from Human and Rat CB$_2$ Receptors

The methods of Felder et al. (*Mol. Pharmaocol.* 48:443-450, 1995) were utilized with minor modifications. Specifically, membrane homogenates from cells stably or transiently expressing the human or rat CB$_2$ receptor were washed by centrifugation and diluted into a 50 mM Tris HCl (pH 7.4), 5 mM MgCl$_2$, 2.5 mM EDTA, and 0.1% BSA buffer. Specific binding of 3H-CP55940 was defined with 1 µM CP55940. The ability of compounds to displace specific 3H-CP55940 binding was tested over a range of concentrations in the Tris, MgCl$_2$, EDTA, BSA buffer in the presence of 1% dimethyl sulfoxide by incubating at room temperature for 90 minutes in a volume of 300 µl. Unifilter 96-well microplates pretreated with 0.5% polyvinylpyrrolidone, 0.1% polysorbate 20 in water were washed three times with cold Tris buffer. The reaction mixture was then transferred to the filter plate immediately before terminating the incubation by rapid filtration and three 200 µl washes with cold Tris buffer. After the filter plates dried, microscint 20 was added to each well, the plate sealed and counted for determination of disintegrations per minute. The displacement curves were graphed and the resulting Ki values determined utilizing Graphpad Prism.

Example 76 has a human receptor Ki value of 33.9 nM and a rat receptor Ki value of 31.3 nM.

Thus, the compounds of the present invention are shown to bind to both human and rat CB$_2$ receptors in vitro.

Monoiodoacetate (MIA) Model

For all studies male Lewis rats of approximately 8 weeks of age at the time of MIA injection are used to measure pain in the MIA model. The rats are housed in groups of 2 or 3 per cage and maintained in a constant temperature and on a 12 hour light/12 hour dark cycle. Animals have free access to food and water at all times except during data collection.

In the standard MIA model the right knees of each rat are injected with 0.3 mg MIA in 50 ul of saline and the left knees with 50 ul of saline. Pain is measured at varying times after MIA injection (not normally before 10 day post MIA injection) using incapacitance testing. This measures the difference in hind paw weight bearing between the MIA and saline injected knees, and each measurement is the average of 3 separate measurements each measured over 1 second.

For studies with CB$_2$ agonists rats are randomized into dose groups (n=5 or 6) and then dosed once with the compound under investigation. Dosing is staggered by 15 minutes for each rat and at a predetermined time post-dose (usually 2 hours), pain measured using incapacitance testing. Studies are routinely run with 4 groups, vehicle (1% carboxy methyl cellulose in water plus 0.25% polysorbate 80) and 3 compound groups which can be either single compounds at a single dose or the same compound at 3 doses. Results are reported as the difference in weight bearing between saline and MIA injected knees and statistical comparisons are made between vehicle treated and compound treated animals to assess the effect of compounds on knee pain in the model.

Example 88 was tested essentially as described above and found to significantly reduce pain versus vehicle at oral doses of 0.3 and 1 mg/kg.

Thus, the compounds of the present invention are shown to be useful in the treatment of pain, in particular joint pain.

We claim:

1. A compound of the formula:

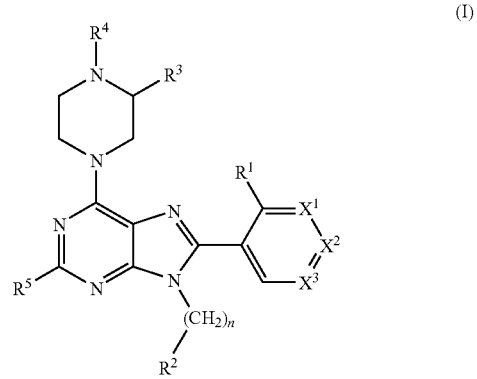

(I)

wherein;

R$^1$ is selected from H, F, Cl, C$_1$-C$_2$ alkyl, CF$_3$, cyclopropyl, OCH$_3$, OCF$_3$ and CN;

R$^2$ is selected from tetrahydrofuranyl, tetrahydropyranyl, azetidinyl-1-carboxylic acid methyl ester and tetrahydrothiophenyl-1,1-dioxide;

R$^3$ is H or combines with R$^4$ together with the atoms to which they are attached to form a fused pyrrolidin-2-one;

R⁴ is selected from C₁-C₂ alkyl, C₁-C₂ fluoroalkyl, cyclopropyl and COCH₃;
R⁵ is selected from H, CH₃ and CF₃;
n is 0 or 1;
X¹ and X³ are independently selected from N, CH and CR⁶;
X² is selected from CH and CR⁶;
with the proviso that only one of X¹, X² and X³ may be other than CH;
R⁶ is selected from F, Cl, CF₃, OCH₃ and OCF₃;
or a pharmaceutically acceptable salt thereof.

2. A compound according to claim 1, or a pharmaceutically acceptable salt thereof, wherein R¹ is selected from Cl, C₁-C₂ alkyl, CF₃, cyclopropyl and OCF₃.

3. A compound according to claim 1, or a pharmaceutically acceptable salt thereof, wherein R¹ is Cl.

4. A compound according to claim 2, or a pharmaceutically acceptable salt thereof, wherein R² is selected from tetrahydrofuranyl and tetrahydropyranyl.

5. A compound according to claim 4, or a pharmaceutically acceptable salt thereof, wherein n is 0.

6. A compound according to claim 2, or a pharmaceutically acceptable salt thereof, wherein R⁴ is selected from C₁-C₂ alkyl, C₁-C₂ fluoroalkyl or cyclopropyl.

7. A compound according to claim 2, or a pharmaceutically acceptable salt thereof, wherein R⁴ is C₁-C₂ alky.

8. A compound according to claim 7, or a pharmaceutically acceptable salt thereof, wherein R³ is H.

9. A compound according to claim 2, or a pharmaceutically acceptable salt thereof, wherein R⁵ is CH₃.

10. A compound according to claim 2, or a pharmaceutically acceptable salt thereof, wherein X¹, X² and X³ are independently selected from CH and CR⁶ where R⁶ is selected from Cl, CF₃, OCH₃ and OCF₃.

11. A compound according to claim 2, or a pharmaceutically acceptable salt thereof, wherein X¹, X² and X³ are each CH.

12. A compound according to claim 1 selected from 8-(2-Chloro-pyridin-3-yl)-2-methyl-6-(4-methyl-piperazin-1-yl)-9-(R)-tetrahydro-furan-3-yl-9H-purine; 2-Methyl-6-(4-methyl-piperazin-1-yl)-9-(tetrahydro-pyran-4-yl)-8-(2-trifluoromethyl-phenyl)-9H-purine; 2-Methyl-6-(4-methyl-piperazin-1-yl)-9-(R)-tetrahydro-furan-3-yl-8-(2-trifluoromethyl-phenyl)-9H-purine; 2-Methyl-6-(4-methyl-piperazin-1-yl)-9-(R)-tetrahydro-furan-3-yl-8-o-tolyl-9H-purine; 8-(2-Chloro-phenyl)-2-methyl-6-(4-methyl-piperazin-1-yl)-9-(S)-tetrahydro-furan-3-yl-9H-purine; 8-(2-Chloro-phenyl)-2-methyl-6-(4-methyl-piperazin-1-yl)-9-(R)-tetrahydro-furan-3-yl-9H-purine; 8-(2-Chloro-phenyl)-2-methyl-6-(4-methyl-piperazin-1-yl)-9-(tetrahydro-pyran-4-yl)-9H-purine; and 8-(2-Chloro-phenyl)-6-(4-ethyl-piperazin-1-yl)-2-methyl-9-(tetrahydro-pyran-4-ylmethyl)-9H-purine; or a pharmaceutically acceptable salt thereof.

13. A compound according to claim 1 being 8-(2-Chloro-phenyl)-2-methyl-6-(4-methyl-piperazin-1-yl)-9-(tetrahydro-pyran-4-yl)-9H-purine; or a pharmaceutically acceptable salt thereof.

14. A pharmaceutical composition comprising a compound of the formula:

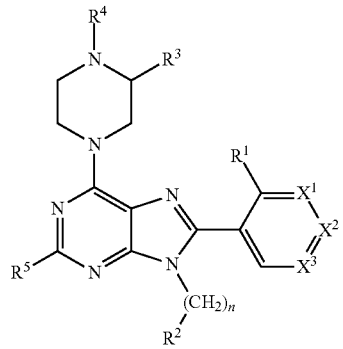

wherein;
R¹ is selected from H, F, Cl, C₁-C₂ alkyl, CF₃, cyclopropyl, OCH₃, OCF₃ and CN;
R² is selected from tetrahydrofuranyl, tetrahydropyranyl, azetidinyl-1-carboxylic acid methyl ester and tetrahydrothiophenyl-1,1-dioxide;
R³ is H or combines with R⁴ together with the atoms to which they are attached to form a fused pyrrolidin-2-one;
R⁴ is selected from C₁-C₂ alkyl, C₁-C₂ fluoroalkyl, cyclopropyl and COCH₃;
R⁵ is selected from H, CH₃ and CF₃;
n is 0 or 1;
X¹ and X³ are independently selected from N, CH and CR⁶;
X² is selected from CH and CR⁶;
with the proviso that only one of X¹, X² and X³ may be other than CH;
R⁶ is selected from F, Cl, CF₃, OCH₃ and OCF₃₁
or a pharmaceutically acceptable salt thereof, and a pharmaceutically acceptable diluent or carrier.

15. A method for the treatment of pain, which comprises administering an effective amount of a compound of the formula:

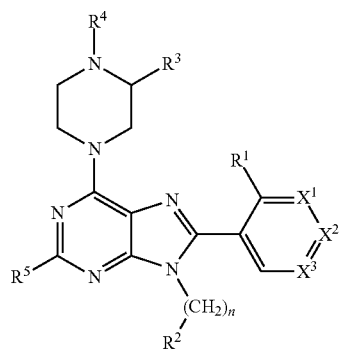

wherein;
R¹ is selected from H, F, Cl, C₁-C₂ alkyl, CF₃, cyclopropyl, OCH₃ OCF₃ and CN;
R² is selected from tetrahydrofuranyl, tetrahydropyranyl, azetidinyl-1-carboxylic acid methyl ester and tetrahydrothiophenyl-1,1-dioxide;
R³ is H or combines with R⁴ together with the atoms to which they are attached to form a fused pyrrolidin-2-one;

$R^4$ is selected from $C_1$-$C_2$ alkyl, $C_1$-$C_2$ fluoroalkyl, cyclopropyl and $COCH_3$;
$R^5$ is selected from H, $CH_3$ and $CF_3$;
n is 0 or 1;
$X^1$ and $X^3$ are independently selected from N, CH and $CR^6$;
$X^2$ is selected from CH and $CR^6$;
with the proviso that only one of $X^1$, $X^2$ and $X^3$ may be other than CH;
$R^6$ is selected from F, Cl, $CF_3$, $OCH_3$ and $OCF_3$;
or a pharmaceutically acceptable salt thereof, to a human being or animal in need thereof.

16. A method according to claim 15 for the treatment of osteoarthritic pain.

17. The pharmaceutical composition according to claim 14 where the compound is 8 (2 Chloro-phenyl)-2-methyl-6-(4-methyl-piperazin-1-yl)-9-(tetrahydro-pyran-4-yl)-9H-purine, or a pharmaceutically acceptable salt thereof.

18. The method according to claim 15 where the compound is 8-(2-Chloro-phenyl)-2-methyl-6-(4-methyl-piperazin-1-yl)-9-(tetrahydro-pyran-4-yl)-9H-purine, or a pharmaceutically acceptable salt thereof.

19. The method according to claim 18, wherein the pain is osteoarthritic pain.

* * * * *

UNITED STATES PATENT AND TRADEMARK OFFICE
CERTIFICATE OF CORRECTION

PATENT NO. : 8,252,798 B2
APPLICATION NO. : 12/633812
DATED : August 28, 2012
INVENTOR(S) : Peter Charles Astles et al.

It is certified that error appears in the above-identified patent and that said Letters Patent is hereby corrected as shown below:

Column 1, Line 3, delete "applicaton" and insert -- application --

Column 89, Line 30, In Claim 7, delete "alky." and insert -- alkyl. --

Column 90, Line 34 (Approx.), In Claim 14, delete "$OCF_{31}$" and insert -- $OCF_3$; --

Column 92, Line 2, In Claim 17, delete "8 (2 Chloro" and insert -- 8-(2-Chloro --

Signed and Sealed this
Twenty-seventh Day of November, 2012

David J. Kappos
*Director of the United States Patent and Trademark Office*